(12) United States Patent
Willard et al.

(10) Patent No.: US 11,266,463 B2
(45) Date of Patent: *Mar. 8, 2022

(54) DEVICES AND METHODS FOR NERVE MODULATION

(71) Applicant: BOSTON SCIENTIFIC SCIMED, INC., Maple Grove, MN (US)

(72) Inventors: Martin R. Willard, Burnsville, MN (US); Patrick A. Haverkost, Corcoran, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/865,633

(22) Filed: May 4, 2020

(65) Prior Publication Data

US 2020/0261151 A1 Aug. 20, 2020

Related U.S. Application Data

(63) Continuation of application No. 14/327,154, filed on Jul. 9, 2014, now Pat. No. 10,660,698.

(60) Provisional application No. 61/845,289, filed on Jul. 11, 2013.

(51) Int. Cl.
*A61B 18/14* (2006.01)
*A61M 25/10* (2013.01)
*A61N 1/36* (2006.01)
*A61B 18/00* (2006.01)
*A61M 25/06* (2006.01)

(52) U.S. Cl.
CPC ......... *A61B 18/1492* (2013.01); *A61M 25/10* (2013.01); *A61N 1/3606* (2013.01); *A61B 2018/00101* (2013.01); *A61B 2018/00267* (2013.01); *A61B 2018/00404* (2013.01); *A61B 2018/00434* (2013.01); *A61B 2018/00511* (2013.01); *A61B 2018/00791* (2013.01); *A61B 2018/00797* (2013.01); *A61B 2018/00821* (2013.01); *A61M 2025/0681* (2013.01)

(58) Field of Classification Search
CPC ...... A61B 18/1492; A61B 2018/00101; A61B 2018/00267; A61B 2018/00404; A61B 2018/00434; A61B 2018/00511; A61M 25/10
See application file for complete search history.

(56) References Cited

U.S. PATENT DOCUMENTS

| | | | |
|---|---|---|---|
| 6,251,109 B1 * | 6/2001 | Hassett | A61B 18/1492 606/45 |
| 2006/0129143 A1 * | 6/2006 | Flaxmeier | A61B 18/1492 606/29 |
| 2008/0161801 A1 * | 7/2008 | Steinke | A61B 18/18 606/41 |

(Continued)

*Primary Examiner* — Michael F Peffley
*Assistant Examiner* — Bo Ouyang
(74) *Attorney, Agent, or Firm* — Kacvinsky Daisak Bluni PLLC

(57) ABSTRACT

Systems for nerve and tissue modulation are disclosed. An illustrative system may include an intravascular nerve modulation system including a catheter shaft, an expandable basket and one or more electrode assemblies affixed to the expandable basket. The one or more electrode assemblies may be affixed to the expandable basket using one or more covers or coatings.

17 Claims, 13 Drawing Sheets

(56) References Cited

U.S. PATENT DOCUMENTS

2012/0071870 A1\* 3/2012 Salahieh ................ A61B 5/287
606/33

\* cited by examiner

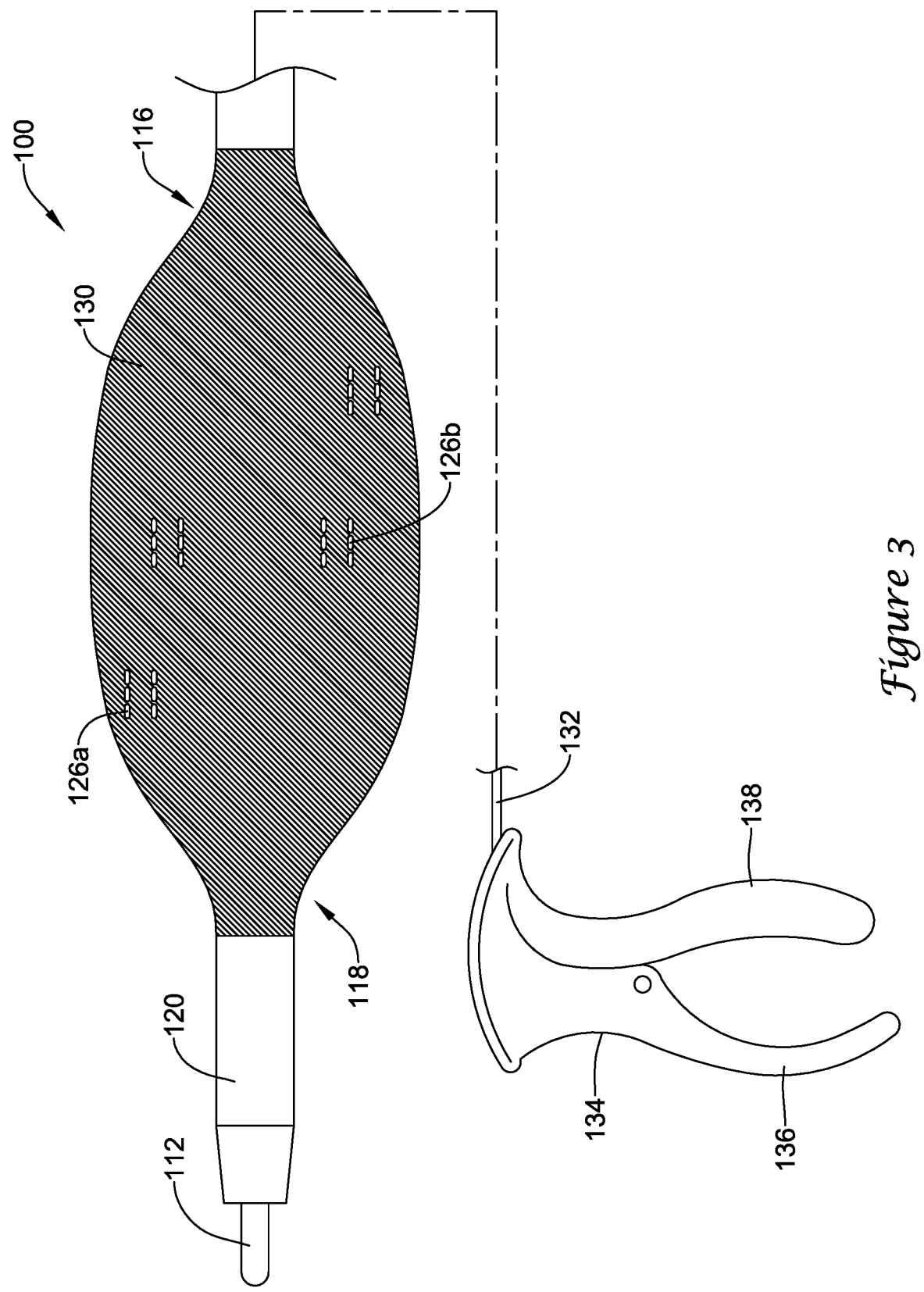

DEVICES AND METHODS FOR NERVE MODULATION

CROSS-REFERENCE TO RELATED APPLICATIONS

This application is a continuation of U.S. patent application Ser. No. 14/327,154, filed Jul. 9, 2014, which claims priority under 35 U.S.C. § 119 to U.S. Provisional Application Ser. No. 61/845,289, filed Jul. 11, 2013, the disclosures of which are incorporated herein by reference in their entirety.

FIELD

The invention generally pertains to percutaneous and intravascular devices for nerve modulation and/or ablation.

BACKGROUND

Certain treatments involve, and in some cases require, the temporary or permanent interruption or modification of select nerve function. One example treatment is renal nerve ablation, which can be used to treat conditions related to congestive heart failure. The kidneys produce a sympathetic response to congestive heart failure, which, among other effects, increases the undesired retention of water and/or sodium. Ablating some of the nerves running to the kidneys may reduce or eliminate this sympathetic function, which may provide a corresponding reduction in the associated undesired symptoms.

Many body tissues, such as nerves, including renal nerves, brain tissue, cardiac tissue and the tissue of other body organs, are in close proximity to blood vessels and/or other body cavities. This proximity enables the tissues to be accessed percutaneously or intravascularly through walls of the blood vessels. In some instances, it may be desirable to ablate perivascular nerves using a radio frequency (RF) electrode. In other instances, the perivascular nerves may be ablated by other techniques, including procedures that apply thermal, ultrasonic, laser, microwave, and/or other related energy sources to the vessel wall.

It may be beneficial to provide apparatuses and methods including, but not limited to, renal nerve modulation systems as well as methods of use and manufacture thereof, that increase and/or otherwise enhance the efficacy of the electrical energy delivered within an intended treatment zone of a patient's body.

SUMMARY

The present disclosure is directed to an intravascular nerve modulation system for performing nerve ablation.

Accordingly, one illustrative embodiment includes an intravascular nerve modulation system having an outer elongate shaft having a proximal end, a distal end, and a lumen extending therebetween and an inner elongate shaft having a proximal end and a distal end. The system may further include an expandable basket having a proximal end and a distal end. The proximal end of the expandable basket may be affixed adjacent to the distal end of the outer elongate shaft. An electrode assembly may be affixed to an outer surface of the expandable basket and an outer cover may be disposed over the outer surface of the expandable basket and at least a portion of the electrode assembly. In some embodiments, the distal end of the basket may be affixed to or adjacent to the distal end of the inner tubular such that in an expanded configuration, the distal end of the expandable basket and the proximal end of the expandable basket may have a tapered cross-sectional area. In other embodiments, in an expanded configuration the distal end of the expandable basket may have a larger cross-sectional area than the proximal end of the expandable basket.

The above summary of some embodiments is not intended to describe each disclosed embodiment or every implementation of the present disclosure. The Figures, and Detailed Description, which follow, more particularly exemplify these embodiments.

BRIEF DESCRIPTION OF DRAWINGS

The invention may be more completely understood in consideration of the following detailed description of various embodiments in connection with the accompanying drawings, in which:

FIG. 3 illustrates the illustrative renal nerve modulation device of FIGS. 2A-2D including an actuation mechanism.

Figure 1:
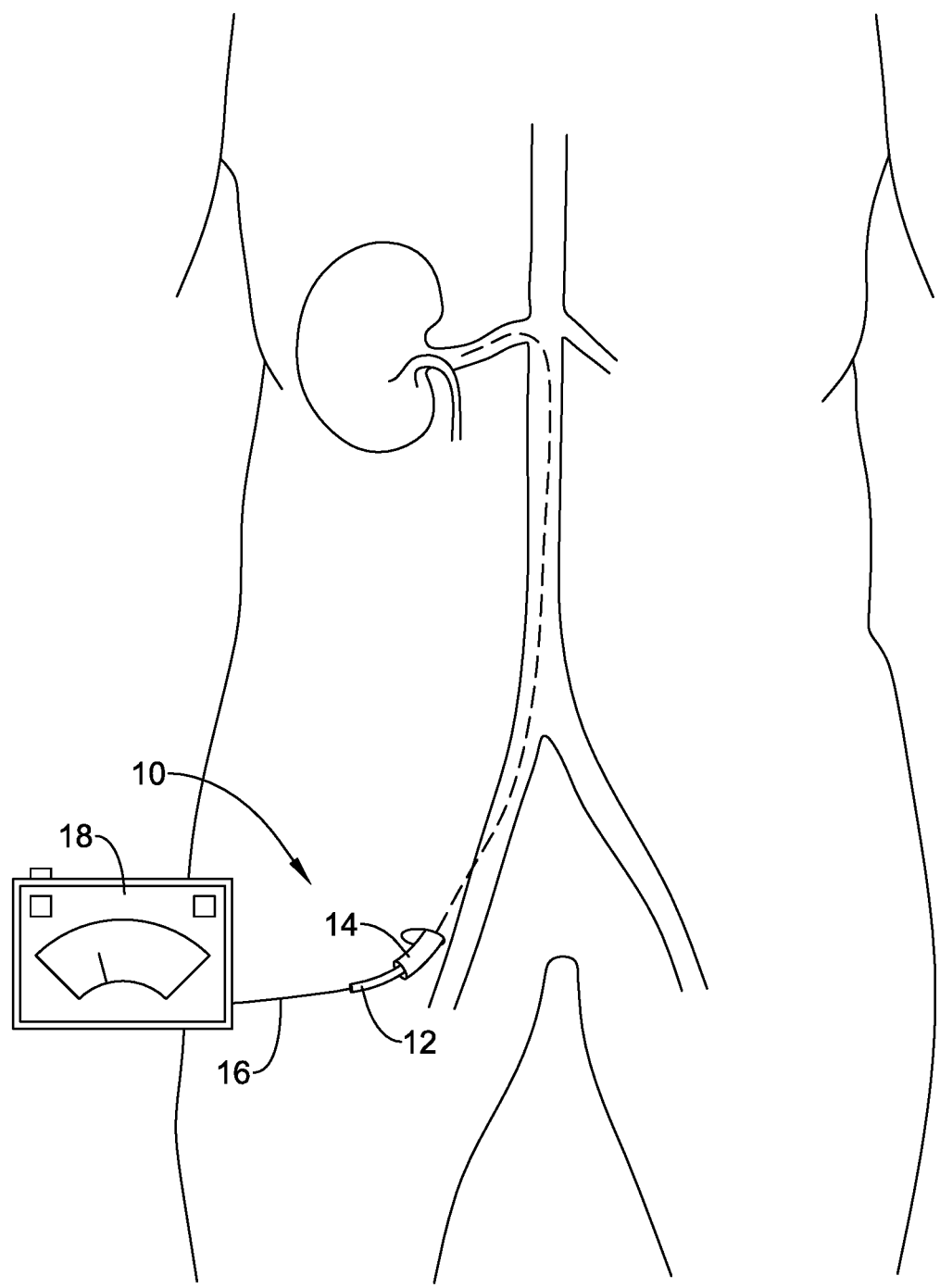
FIG. 1 is a schematic view illustrating a renal nerve modulation system in situ.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

The following description should be read with reference to the drawings, wherein like reference numerals indicate like elements throughout the several views. The drawings, which are not necessarily to scale, are not intended to limit the scope of the claimed invention. The detailed description and drawings illustrate exemplary embodiments of the claimed invention.

All numbers used or otherwise included herein should be considered to be modified by the term "about." The disclosure or recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular indefinite articles "a," "an," and the definite article "the," should be considered to include or otherwise cover both single and plural referents, unless the content clearly dictates otherwise. In other words, these articles are applicable to one or more referents. As used in this specification and the appended claims, the term "or" should be considered to mean "and/or," unless the content clearly dictates otherwise.

References in the specification to "an embodiment," "some embodiments," "other embodiments," etc., indicate that the embodiment described may include a particular feature, structure, or characteristic, but every embodiment may not necessarily include the particular feature, structure, or characteristic. Moreover, such phrases do not necessarily refer to the same embodiment. Further, if a particular feature, structure, or characteristic is described in connection with an embodiment, then it would be within the knowledge of one skilled in the art to affect such feature, structure, or characteristic in connection with other embodiments, whether or not explicitly described, unless clearly stated to the contrary.

Certain treatments require the temporary or permanent interruption or modification of select nerve function. One example treatment is renal nerve ablation, which is sometimes used to treat conditions related to hypertension, congestive heart failure, diabetes, or other conditions impacted by high blood pressure or salt retention. The kidneys produce a sympathetic response to congestive heart failure, which, among other effects, increases the undesired retention of water and/or sodium. Ablating some of the nerves running to the kidneys may reduce or eliminate this sympathetic function, which may provide a corresponding reduction in the associated undesired symptoms.

Many of the devices and methods are disclosed herein in the context of renal nerve modulation through a blood vessel wall. However, devices and methods of other embodiments may be used in other contexts, such as applications other than where nerve modulation and/or ablation are desired. It is contemplated that the devices and methods may be used in other treatment locations and/or applications where nerve modulation and/or other tissue modulation including heating, activation, blocking, disrupting, or ablation are desired, such as, but not limited to: blood vessels, urinary vessels, or in other tissues via trocar and cannula access. For example, the devices and methods described herein can be applied to hyperplastic tissue ablation, cardiac ablation, pulmonary vein isolation, tumor ablation, benign prostatic hyperplasia therapy, nerve excitation or blocking or ablation, modulation of muscle activity, hyperthermia or other warming of tissues, etc. The disclosed methods and apparatus can be applied to any relevant medical procedure, involving both human and non-human subjects. The term modulation refers to ablation and other techniques that may alter the function of affected nerves and other tissue. In some embodiments, a single ablation device may be used to sequentially or simultaneously perform multiple ablations, if desired.

FIG. 1 is a schematic view of an illustrative renal nerve modulation system in situ. The renal nerve modulation system 10 may include one or more conductive element(s) 16 for providing power to a renal nerve modulation device. An illustrative renal nerve modulation device may include an intravascular catheter or nerve modulation device 12 optionally disposed within a delivery sheath or guide catheter 14. The delivery sheath 14 may be adapted to slidably contain the intravascular catheter 12 if a radially expanding distal portion (not shown) of the intravascular catheter 12 is in a non-expanded configuration, as will be discussed in more detail below. A distal end of each of the conductive element(s) 16 is attached to one or more electrodes at a location at or near a distal end of the intravascular catheter 12. A proximal end of each of the conductive element(s) 16 may be connected to a power and control unit 18, which supplies electrical energy used to activate the one or more electrodes. The power and control unit 18 is typically located outside of the patient's body. The electrodes are capable of modulating or ablating tissue upon being suitably activated via the control unit 18.

In the following disclosure, the terms electrode and electrodes may be considered to be equivalent to elements capable of ablating adjacent tissue. The disclosure of "adjacent tissue" is intended to cover any tissue located sufficiently proximate the electrode(s) for ablation, and the locations and distances involved are intended to vary depending on application and/or other factors.

The power and control unit 18 may include monitoring elements to monitor parameters, such as power, temperature, voltage, pulse size, impedance and/or shape, and/or other suitable parameters. The power and control unit 18 may also include, or otherwise be used with, sensors mounted along the renal nerve modulation device, as well as suitable controls for performing the desired procedure. In some embodiments, the control unit 18 may control a radio frequency (RF) electrode. The electrode may be configured to operate at a frequency of approximately 460 kHz. However, any desired frequency in the RF range may be used, for example, from 450-500 kHz. In addition, other types of ablation devices may be used as desired including, but not limited to, devices that involve resistance heating, ultrasound, microwave, and laser technologies. The power and control unit 18 may supply different forms of power to these devices.

Figure 2A:
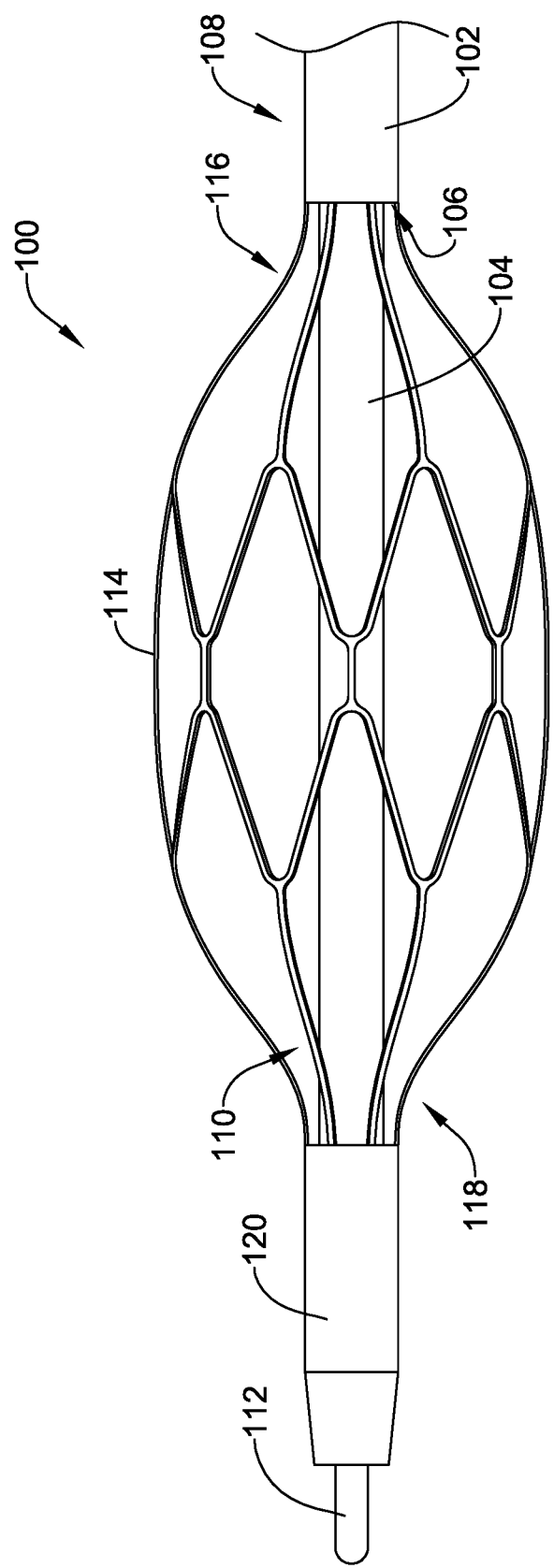
FIGS. 2A-2D illustrate a distal portion of an illustrative renal nerve modulation device.

FIGS. 2A-2D and 3 illustrate a distal portion of an illustrative renal nerve modulation device 100 having a basket structure covered with a coating. Referring first to FIG. 2A, the renal nerve modulation system 100 may include a catheter shaft having an outer elongate shaft 102 and an inner elongate shaft 104. The outer elongate shaft 102 may extend proximally from a distal end region 108 to the proximal end configured to remain outside of a patient's body. The inner elongate shaft 104 may be slidably disposed within a lumen 106 of the outer elongate shaft 102. The inner elongate shaft 104 may extend proximally from a distal end region 110 to a proximal end configured to remain outside of a patient's body. Although not shown, the proximal ends of the inner and/or outer elongate shafts 104, 102 may include a hub attached thereto for connecting other treatment devices or providing a port for facilitating other treatments. It is contemplated that the stiffness of the inner and/or outer elongate shafts 104, 102 may be modified to form a modulation device 100 for use in various vessel diameters and various locations within the vascular tree.

In some instances, the inner and/or outer elongate shafts 104, 102 may have an elongate tubular structure and may include one or more lumens extending therethrough. For instance, in the illustrated embodiment, the outer elongate shaft 102 may include a lumen 106 for slidably receiving the inner tubular shaft 104. The inner tubular shaft 104 may include a lumen (not explicitly shown) having a guidewire wire 112 slidably disposed therein. In some instances, the modulation device 100 may have a fixed wire distal end with no guidewire lumen. These are just examples. In some embodiments, the inner and/or outer elongate shafts 104, 102 may include one or more auxiliary lumens. In some instances, the inner and/or outer elongate shafts 104, 102 may include a separate lumen(s) (not shown) for infusion of fluids, such as saline or dye for visualization or for other purposes such as the introduction of a medical device, and so forth. The fluid may facilitate cooling of the modulation device 100 during the ablation procedure, in addition to the cooling of a body lumen. Further, the lumens may be configured in any way known in the art. For example, the lumen(s) may extend along the entire length of the inner and/or outer elongate shafts 104, 102 such as in an over-the-wire catheter or may extend only along a distal portion of the inner and/or outer elongate shafts 104, 102 such as in a single operator exchange (SOE) catheter. These examples are not intended to be limiting, but rather examples of some possible configurations. While not explicitly shown, the modulation device 100 may further include temperature sensors/wire, an infusion lumen, radiopaque marker bands, fixed guidewire tip, a guidewire lumen, and/or other components to facilitate the use and advancement of the device 100 within the vasculature.

Further, the inner and/or outer elongate shafts 104, 102 may have a relatively long, thin, flexible tubular configuration. In some instances, the inner and/or outer elongate shafts 104, 102 may have a generally circular cross-section, however, other suitable configurations such as, but not limited to, rectangular, oval, irregular, or the like may also be contemplated. In addition, the inner and/or outer elongate shafts 104, 102 may have a cross-sectional configuration adapted to be received in a desired vessel, such as a renal artery. For instance, the inner and/or outer elongate shafts 104, 102 may be sized and configured to accommodate passage through an intravascular path, which leads from a percutaneous access site in, for example, the femoral, brachial, or radial artery, to a targeted treatment site, for example, within a renal artery.

The modulation device 100 may further include an expandable basket 114 having a proximal end 116 and a distal end 118. In the expanded form, the basket 114 may have a tapered proximal end 116 and a tapered distal end 118 and an enlarged central region, although this is not required. In some embodiments, the expandable basket 114 may be laser cut from a generally tubular member to form the desired pattern. While the expandable basket 114 is illustrated as having an open cell, generally stent-like, structure it is contemplated that the basket 114 may be formed to have any of a number of different configurations. For example, in some instances, the basket 114 may be formed from a number of generally longitudinally extending tines or may be formed from one or more filaments that may be woven, braided, knotted, etc. These are just examples. It is contemplated that the use of an expandable basket 114 may eliminate the need for an inflation lumen, thus reducing the overall profile of the modulation system 100.

It is contemplated that the expandable basket 114 can be made from a number of different materials such as, but not limited to, metals, metal alloys, shape memory alloys and/or polymers, as desired, enabling the basket 114 to be expanded into shape when positioned within the body. For example, the expandable basket 114 can be formed from alloys such as, but not limited to, nitinol or Elgiloy®. Depending on the material selected for construction, the basket 114 may be self-expanding or may require an actuation mechanism as will be discussed in more detail below. In some embodiments, fibers may be used to make the expandable basket 114, which may be cored fibers, for example, having an outer shell made of nitinol having a platinum core. It is further contemplated the expandable basket 114 may be formed from polymers including, but not limited to, polyether ether ketone (PEEK), nylon, polyethylene terephthalate (PET), polyimides, polyether block amides, etc.

The proximal end 116 of the basket 114 may be secured to or adjacent to the distal end region 108 of the outer elongate shaft 102. The distal end 118 of the basket 114 may be secured to or adjacent to the distal end region 110 of the inner elongate shaft 104. In some instances, the distal end 118 of the basket 114 may be secured directly to the inner elongate shaft 104. In other instances, the distal end 118 of the basket 114 may be secured to a mounting element 120. The mounting element 120 may be slidably disposed over the inner elongate shaft 104 or may be fixedly secured to the inner elongate shaft 104. As noted above, in some instances, the basket 114 may be self-expanding. It is contemplated that a self-expanding basket 114 may be maintained in a compressed (or collapsed state) when an external force is placed on the basket 114. The basket 114 may then expand when the external force is released. In such an instance, the basket 114 may be formed in the expanded state (as shown in FIG. 2A) and compressed to fit within a delivery sheath. Upon reaching the target location, the delivery sheath can be retracted to deploy the expandable basket 114. It is contemplated that in some instances, the basket may be self-expanding without a capture sheath since the guide sheath could introduce it into the vessel and if the cover material made the basket 114 atraumatic enough so that it could be introduced into the artery while expanded.

In other embodiments, the system 100 may include an actuation mechanism, for example, a pull wire 132 (see FIG. 3), which may be employed to manipulate or actuate the expandable basket 114 between the collapsed and expanded configurations. In an embodiment, the pull wire 132 may be attached to the proximal end 116 or distal end 118 of the basket 114 such that a push-pull actuation of the pull wire 132 may manipulate the expandable basket 114, thus actuating the expandable basket 114 between the collapsed and expanded configurations. In some instances, the pull wire 132 may be pulled proximally to pull the expandable basket 114, moving the expandable basket 114 to the expanded configuration. In addition, the pull wire 132 may be pushed distally to move the expandable basket 114 into the collapsed configuration. Alternatively, the pull wire 132 may be pushed distally, which may allow the expandable basket 114 to move to the expanded state. In such an instance, the pull wire 132 may be pulled proximally, which may allow the expandable basket 114 to move to the collapsed state.

Figure 2B:
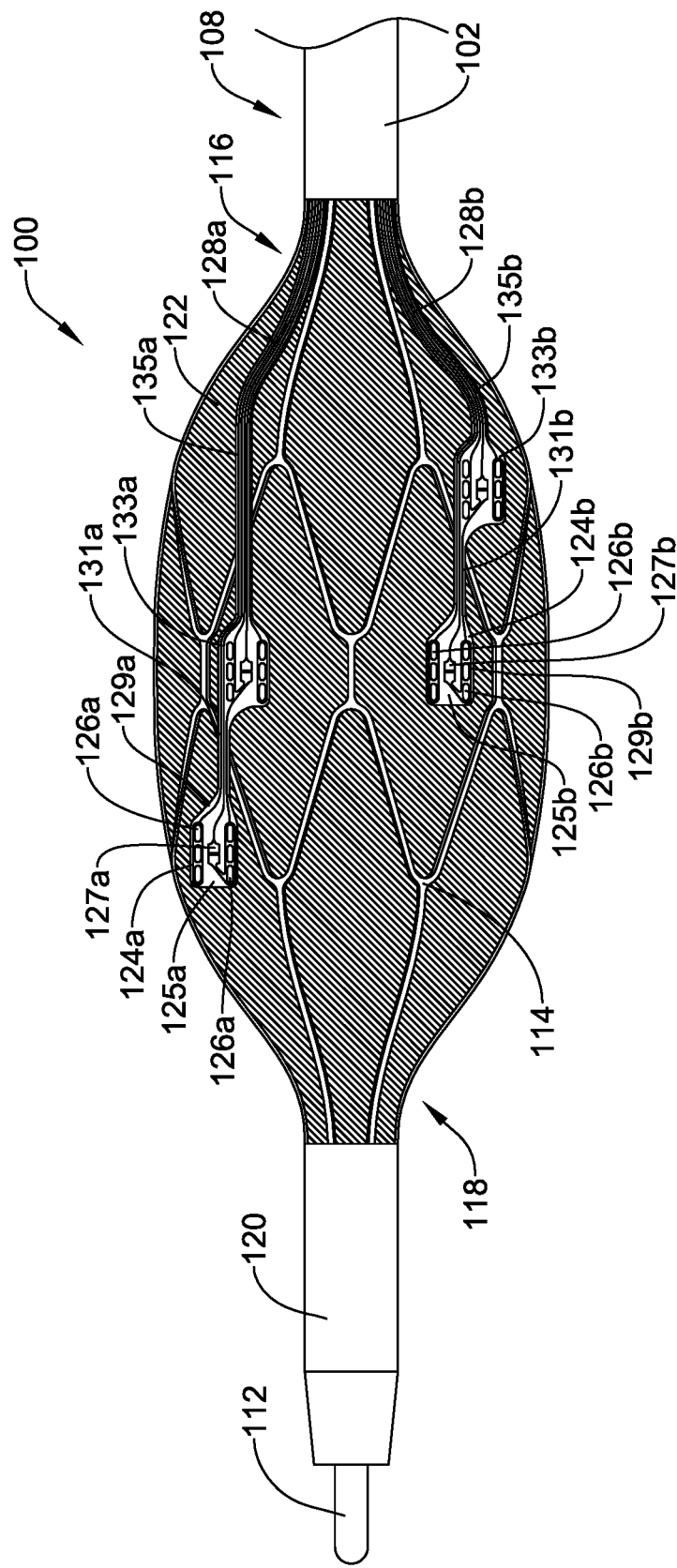

FIG. 2B illustrates the modulation system 100 of FIG. 2A including additional components. The modulation system 100 may further include an inner cover or coating 122 disposed on an inner surface of the expandable basket 114. In some instances, the inner cover 122 may be adhered to the basket 114 using methods commonly known in the art. The inner cover 122 may be made from an elastomeric material, such as, but not limited to: polyurethane, silicone, etc. An elastomeric material may help close the basket 114 to its un-expanded configuration after use. However, in some instances, elastomers such as polyurethane may fail due the heat from ablation. To prevent this, the elastomer could be insulated around the electrodes with a higher temperature material, doped to increase its melt point, (for example, with silica), one may use higher temperature urethanes (for example, aromatics that are dip coated rather than extruded). Alternatively, the cover material could be a less stretchable material, for example, tetrafluoroethylene (Tfe), polyethylene terephthalate (PET), or fabrics (for example, polyester or polymer coated fabrics), which would be less subject to the ablation temperatures. It is contemplated that the inner cover 122 may extend from the proximal end 116 to the distal end 118 of the basket 114. However, this is not required. It is contemplated that the inner cover 122 may extend over any length or partial length of the basket 114 desired, or may not even be present.

The modulation system 100 may further include one or more electrode assemblies 124*a*, 124*b* positioned on a surface of the expandable basket 114 and/or inner cover 122 for delivering RF energy to a desired treatment region. In some instances, one or more electrode assemblies 124*a*, 124*b* may be positioned on a surface of an outer cover 130 (see FIG. 2C). An exemplary electrode assembly useable with the embodiments disclosed herein is disclosed in U.S. Patent Application Ser. No. 61/856,523 entitled "Spiral Bipolar Electrode Renal Denervation Balloon", the full disclosure of which is incorporated by reference herein. Each electrode assembly 124*a*, 124*b* may be constructed as a flexible circuit having a plurality of layers. Such layers may be continuous or non-contiguous, i.e., made up of discrete portions. A base layer 125*a*, 125*b* of insulation may provide a foundation for the electrode assemblies 124*a*, 124*b*. The base layer 125*a*, 125*b* may be constructed from a flexible polymer such as polyimide, although other materials are contemplated. However, the modulation systems disclosed herein are not intended to be limited to the use of only flexible circuits to deliver the treatment energy to the treatment region. It is contemplated that the energy delivery devices may be of any type desired. A conductive layer made up of a plurality of discrete traces may be layered on top of the base layer 125*a*, 125*b*. The conductive layer may be, for example, a layer of electrodeposited copper. Other materials are also contemplated. An insulating layer may be discretely or continuously layered on top of the conductive layer, such that the conductive layer may be fluidly sealed between the base layer 125*a*, 125*b* and the insulating layer. Like the base layer 125*a*, 125*b*, the insulating layer may be constructed from a flexible polymer such as polyimide, although other materials are contemplated. In other embodiments, the insulating layer may be a complete or partial polymer coating, such as PTFE or silicone. Other materials are also contemplated.

The electrode assemblies 124*a*, 124*b* may include a distal electrode pad 129*a*, 129*b*. In this region, the base layer 125*a*, 125*b* may form a rectangular shape. This is not intended to be limiting. Other shapes are contemplated. While not explicitly shown, the electrode assemblies 124*a*, 124*b* may include a plurality of openings to provide for added flexibility, and the pads and other portions of the assemblies may include rounded or curved corners, transitions and other portions. In some instances, the openings and rounded/curved features may enhance the assembly's resistance to delamination from its expandable device, as may occur, in some instances, when the expandable device is repeatedly expanded and collapsed (which may also entail deployment from and withdrawal into a protective sheath), such as may be needed when multiple sites are treated during a procedure. It is contemplated that in some embodiments, the base layer 125*a*, 125*b* may not be required. For example, the electronic components, electrodes and thermistors, could be mounted on the basket 114 or in the inner cover 122 or outer cover 130 (see FIGS. 2C and 2D) and the conductive traces could be fine wires, or could be traced inside the inner cover 122 or outer cover 130 using for example, Micropen technology.

The distal electrode pad 129*a*, 129*b* may include a plurality of discrete traces 128*a*, 128*b* layered on top of the base layer 125*a*, 125*b*. These traces may include a ground trace, an active electrode trace, and a sensor trace (not explicitly shown) for electrically connecting electrodes, components, and/or a power and control unit. The ground trace may include an elongated electrode support laterally offset from a sensor ground pad. The sensor ground pad may be electrically coupled to the elongated support of the ground trace and may be centrally located on the distal electrode pad. A bridge may connect a distal most portion of the sensor ground pad to a distal portion of the elongated electrode support of the ground trace. The bridge may taper down in width as it travels to the sensor ground pad. In some embodiments, the bridge may have a relatively uniform and thin width to enable a desired amount of flexibility. The elongated electrode support may taper down in width at its proximal end; however, this is not required. In some embodiments, the elongated electrode support may abruptly transition to a much thinner trace at its proximal portion, to enable a desired amount of flexibility. The shape and position of the traces may also be optimized to provide dimensional stability to the electrode assembly 124*a*, 124*b* as a whole, so as to prevent distortion during deployment and use. The ground trace and active electrode trace may share a similar construction. The active electrode trace may also include an elongated electrode support.

The ground electrode trace and active electrode trace may include a plurality of electrodes 126*a*, 126*b*. Three electrodes 126*a*, 126*b* may be provided for each electrode trace, however, more or less may be used. Additionally, each electrode 126*a*, 126*b* may have radiused corners to reduce tendency to snag on other devices and/or tissue. Although the above description of the electrodes 126*a*, 126*b* and the traces associated with them has been described in the context of a bi-polar electrode assembly, those of skill in the art will recognize that the same electrode assembly may function in a monopolar mode as well. For instance, as one non-limiting example, the electrodes associated with active electrode traces may be used as monopolar electrodes, with ground trace disconnected during energization of those electrodes.

In some embodiments, the electrodes 126*a*, 126*b* may be gold pads approximately 0.038 mm thick from the conductive layer and that may protrude about 0.025 mm above the insulating layer 125*a*, 125*b*. Without limiting the use of other such suitable materials, gold may be a good electrode material because it is very biocompatible, radiopaque, and electrically and thermally conductive. In other embodiments, the electrode thickness of the conductive layer may range from about 0.030 mm to about 0.051 mm. At such thicknesses, relative stiffness of the electrodes 126*a*, 126*b*, as compared to, for example, the copper conductive layer, may be high. Because of this, using a plurality of electrodes, as opposed to a single electrode, may increase flexibility. In other embodiments, the electrodes may be as small as about 0.5 mm by about 0.2 mm or as large as about 2.2 mm by about 0.6 mm for electrode 126*a*, 126*b*.

The sensor trace may be centrally located on the distal electrode pad 129*a*, 129*b* and may include a sensor power pad facing the sensor ground pad. These pads may connect to power and ground poles of a temperature sensor 127*a*, 127*b*, such as a thermocouple (for example, Type T configuration: Copper/Constantan) or thermistor. The temperature sensor 127*a*, 127*b* may be proximately connected to the sensor power pad and may be distally connected to the sensor ground pad. To help reduce overall thickness, the temperature sensor 127*a*, 127*b* may be positioned within an opening within the base layer 125*a*, 125*b*.

From the distal electrode pad 129*a*, 129*b*, the combined base layer 125*a*, 125*b*, conductive layer, and insulating layer may reduce in lateral width to an intermediate tail 131*a*, 131*b*. Here, the conductive layer may be formed to include an intermediate ground line, intermediate active electrode line, and intermediate sensor line, which may be respectively coextensive traces of the ground trace, active electrode trace, and sensor trace of the distal electrode pad 129*a*, 129*b*.

From the intermediate tail 131*a*, 131*b*, the combined base layer 125*a*, 125*b*, conductive layer 204, and insulating layer 206 may increase in lateral width to form a proximal electrode pad 133a, 133b. The proximal electrode pad 133a, 133b may be constructed similarly to the distal electrode pad 129a, 129b, with the electrode geometry and temperature sensor arrangement being essentially identical, although various differences may be present. However, as shown, the proximal electrode pad 133a, 133b may be laterally offset from the distal electrode pad 129a, 129b with respect to a central axis extending along the intermediate ground line. The intermediate active electrode line and intermediate sensor line may be laterally coextensive with the proximal electrode pad 133a, 133b on parallel respective axes with respect to the central axis.

From the proximal electrode pad 133a, 133b, the combined base layer 125a, 125b, conductive layer, and insulating layer may reduce in lateral width to form a proximal tail 135a, 135b. The proximal tail 135a, 135b may include a proximal ground line, proximal active electrode line, and proximal sensor line, as well the intermediate active electrode line and intermediate sensor line. The proximal tail 135a, 135b may include connectors (not shown) to enable coupling to one or more sub-wiring harnesses and/or connectors and ultimately to a power and control unit. Each of these lines may be extended along parallel respective axes with respect to the central axis.

As shown, the electrode assembly 124a, 124b may have an asymmetric arrangement of the distal electrode pad 129a, 129b and proximal electrode pad 133a, 133b, about a central axis. Further, the ground electrodes of both electrode pads may be substantially aligned along the central axis, along with the intermediate and proximal ground lines. It has been found that this arrangement may present certain advantages. For example, by essentially sharing the same ground trace, the width of the proximal tail may be only about one and a half times that of the intermediate tail 131a, 131b, rather than being approximately twice as wide if each electrode pad had independent ground lines. Thus, the proximal tail 135a, 135b may be narrower than two of the intermediate tails 131a, 131b.

Further, arranging the electrode pads to share a ground trace may allow control of which electrodes will interact with each other. The various electrode pads may be fired and controlled using solid state relays and multiplexing with a firing time ranging from about 100 microseconds to about 200 milliseconds or about 10 milliseconds to about 50 milliseconds. For practical purposes, the electrode pads may appear to be simultaneously firing yet stray current between adjacent electrode pads of different electrode assemblies 124a, 124b may be prevented by rapid firing of electrodes in micro bursts. This may be performed such that adjacent electrode pads of different electrode pad assemblies 124a, 124b are fired out of phase with one another. Thus, the electrode pad arrangement of the electrode assembly may allow for short treatment times—about 10 minutes or less of total electrode firing time, with some approximate treatment times being as short as about 10 seconds, with an exemplary embodiment being about 30 seconds. Some benefits of short treatment times may include minimization of post-operative pain caused when nerve tissue is subject to energy treatment, shortened vessel occlusion times, reduced occlusion side effects, and quick cooling of collateral tissues by blood perfusion due to relatively minor heat input to luminal tissue.

Figure 4:
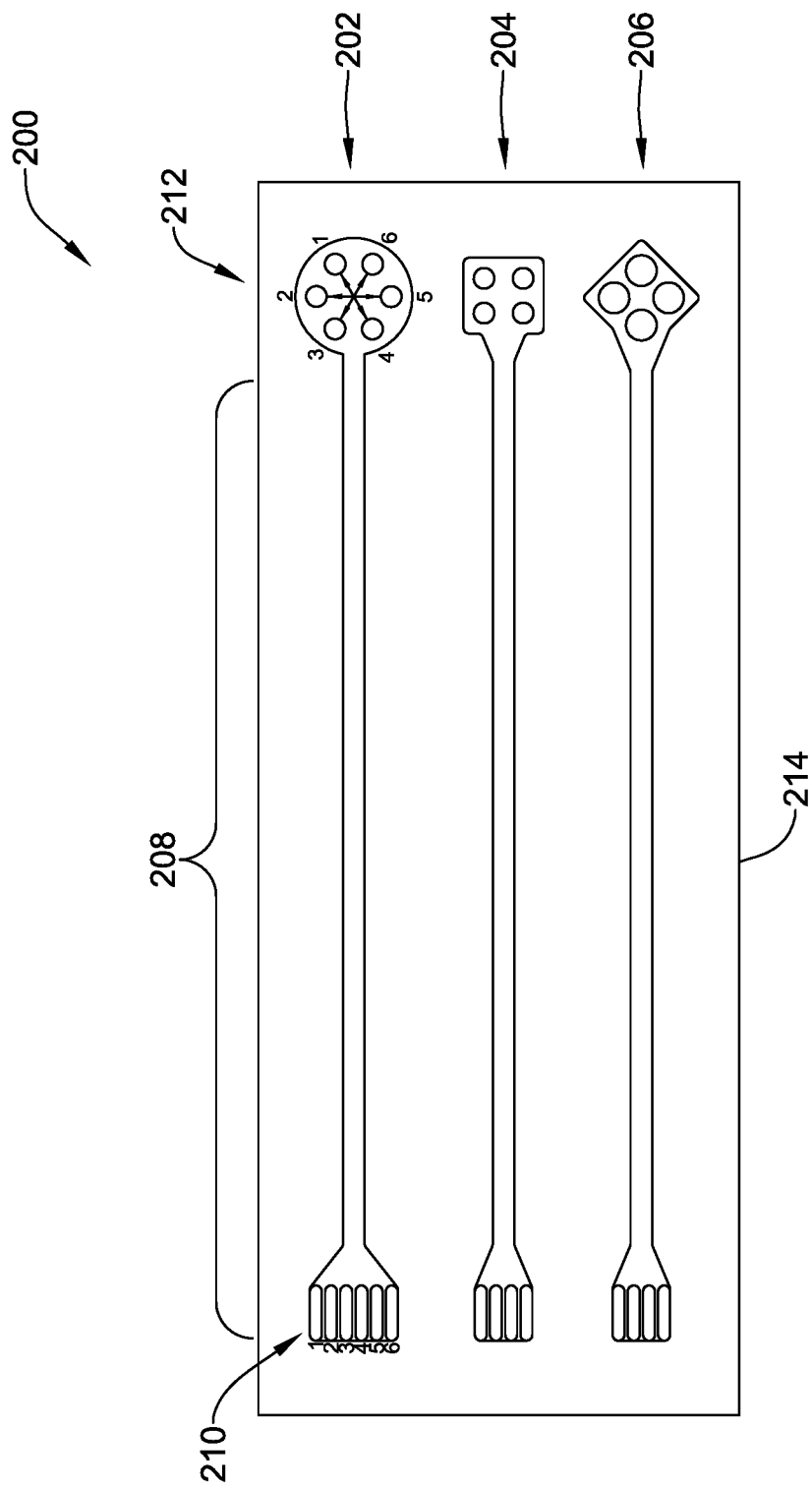
FIG. 4 illustrates some illustrative electrode assemblies.

Referring now to FIG. 4, an illustrative flex circuit panel 200 having flexible circuits 202, 204, and 206 is shown. Each of the flex circuits 202, 204, 206 may include electrically conductive leads 208 that extend between proximal electrical contacts 210 and distal electrodes 212. Leads 208 may be supported by a flexible polymer substrate 214. However, this is not required. It is contemplated that the leads 208, proximal electrical contacts 210, and/or distal electrodes 212 may be mounted directly to any of the expandable baskets or frameworks described herein or to any of the covers or coatings described herein. In some instances, the substrate 214 may be cut around and/or between the electrical components of the circuit to mount the circuits 202, 204, 206 to the desired structure. The electrodes 212 may be positioned adjacent the distal end of a modulation system while the leads 208 may extend proximally along the device such that proximal electrical contact 210 may be electrical coupled to a power and control unit, such as power and control unit 18 shown in FIG. 1. One or more flex circuits 202, 204, and 206 may be mounted to the modulation device. It is contemplated that there may be any number of flex circuits desired based on the desired treatment region and the size of the device. In some instances the electrodes 212 of each flex circuit 202, 204, 206 may optionally provide a grouping or sub-array of electrodes for treating an associated portion or region of a target tissue. Alternative sub-arrays may be provided among electrodes of different flex circuits, may be defined by programmable logic of the processor, and/or may comprise any of a wide variety of alternative electrode circuit structures, with the sub-arrays often being employed for multiplexing or treating the region of target tissue with a plurality of differing electrical energy paths through the tissue.

Still referring to FIG. 4, multiplexing between selected electrodes of an array or sub-array can be effected by selectively energizing electrode pairs, with the target tissue region for the sub-array being disposed between the electrodes of the pairs so that the energy passes therethrough. For example, a pair of electrodes selected from electrodes 1, 2, 3, 4, 5, and 6 of flex circuit 202 (with the selected electrodes optionally being positioned opposite each other) may be energized and then turned off, with another pair then being energized, and so forth. The firing order might be 1 and 4, then 2 and 5, then 3 and 6. Bipolar potentials between the electrodes of the pair can induce current paths in the same general tissue region, with the power dissipated into the tissue optionally remaining substantially constant. This provides a duty cycle of about Vi with respect to heat and/or losses at each electrode surface. The four electrode configurations of flex circuits 204 and 206 could be used in a similar manner with a 50% duty cycle. Monopolar energy might also be applied using a larger ground pad on the skin of the patient or the like, with the duty cycle optionally being cut in half relative to bipolar energy.

Referring again to FIG. 2B, it is contemplated that the modulation system 100 may include any number of electrode assemblies 124a, 124b desired based on the size of the modulation device 100 and/or the desired treatment region. For example, the modulation system may include one, two, three, four, five, or more electrode assemblies. It is further contemplated that the electrode assemblies 124a, 124b may be staggered about the circumference and/or length of the expandable basket 114 such that a maximum number of electrode assemblies 124a, 124b can be positioned on the modulation device.

Figure 2C:
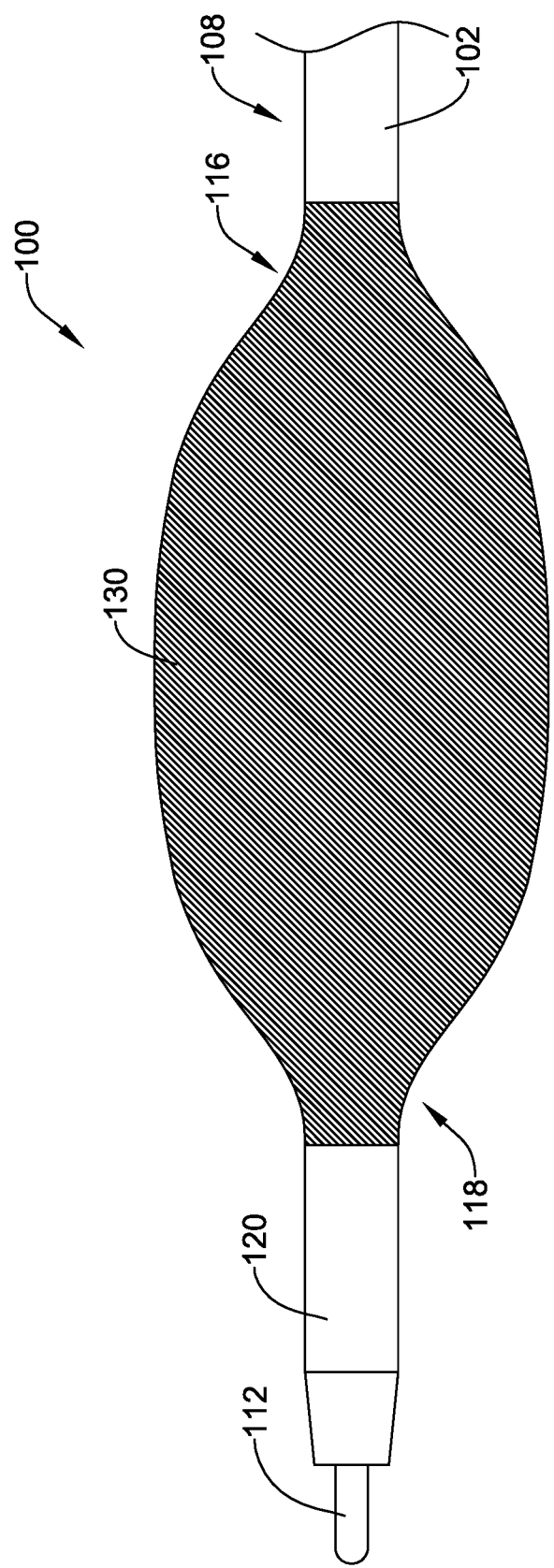

FIG. 2C illustrates the modulation system 100 of FIG. 2B including additional components. The modulation system 100 may further include an outer cover or coating 130 disposed on an outer surface of the expandable basket 114 and over the inner cover 122 when so present. The outer cover 130 may be made from an elastomeric material, such as, but not limited to: polyurethane, silicone, etc. An elastomeric material may help close the basket 114 to its un-expanded configuration after use. However, in some instances, elastomers such as polyurethane may fail due the heat from ablation. To prevent this, the elastomer could be insulated around the electrodes with a higher temperature material, doped to increase its melt point, (for example, silica), or it may be fine using higher temperature urethanes (for example, aromatics that are dip coated rather than extruded). Alternatively, the cover material could be a less stretchable material, for example, tetrafluoroethylene (Tfe), polyethylene terephthalate (PET), or fabrics (for example, polyester or polymer coated fabrics), which would be less subject to the ablation temperatures. It is contemplated that the outer cover 130 may extend from the proximal end 116 to the distal end 118 of the basket 114. However, this is not required. It is contemplated that the outer cover 130 may extend over any length or partial length of the basket 114 desired, or may not even be present. The inner and outer covers 122, 130 may be formed of the same material or may be formed from different materials, as desired. In some embodiments, one or both of the inner and/or outer covers 122, 130 may be omitted.

In some instances, the outer cover 130 may be adhered to the inner cover 122 and/or basket 114 using methods commonly known in the art. Together, the inner and outer covers 122, 130 may encase all or part of the electrode assemblies 124a, 124b and the associated electronics. It is contemplated that the inner and outer covers 122, 130 may fix the electrode assemblies 124a, 124b more securely to the expandable basket 114 relative to securing flex circuits to a traditional inflatable balloon as the inner and outer covers 122, 130 sandwich the electrode assemblies 124a, 124b and may be more amenable to covalent adhesive bonding. It is contemplated that affixing the electrode assemblies 124a, 124b between at least the basket 114 and the outer cover 130 may improve electrode fixation to system since such an arrangement may eliminate or reduce electrode catch points is not dependent on adhesive to fix the electrode assemblies 124a, 124b to the modulation system. This may improve the safety of system 100.

Figure 2D:
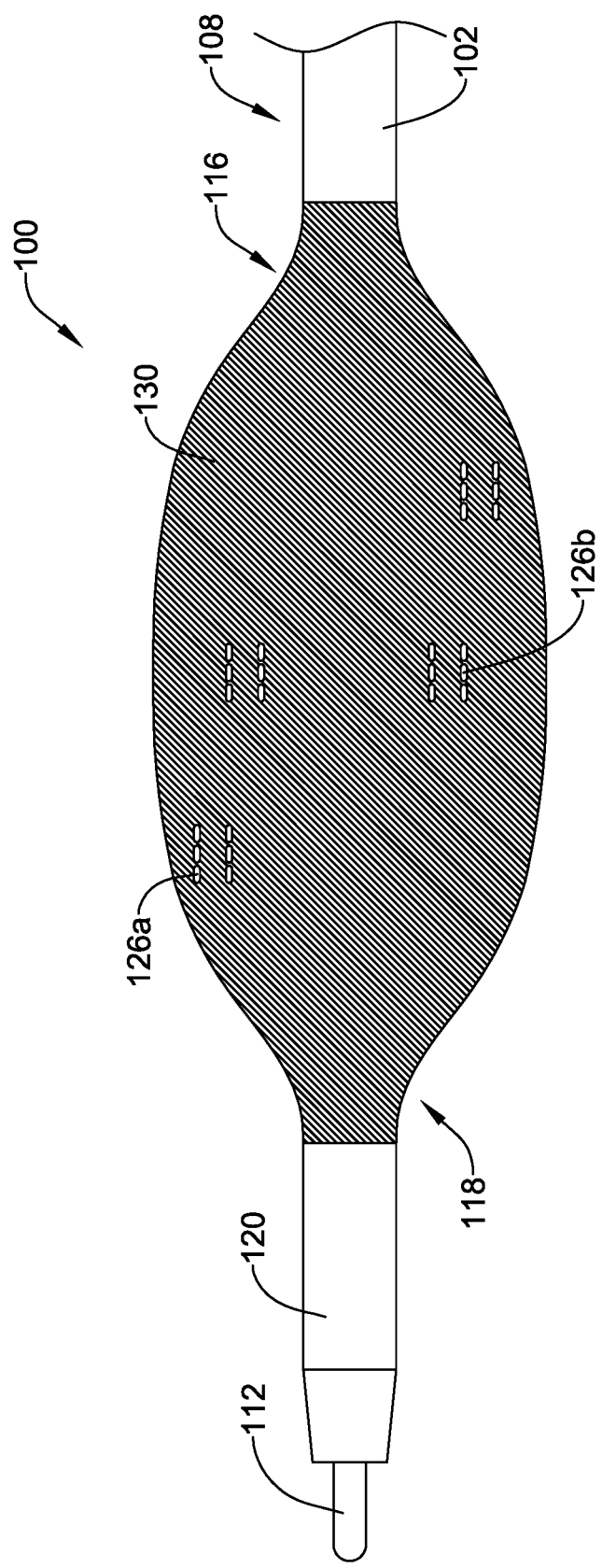

When the outer cover 130 is disposed over the electrodes 126a, 126b, the electrodes may be in insulated contact with the desired treatment region. In some instances, the outer cover 130 may not extend over the electrodes 126a, 126b of the electrode assemblies 124a, 124b, as shown in FIG. 2D. For example, the electrodes 126a, 126b may be coated or covered with a masking material prior to application of the outer cover 130. Once the outer cover 130 has been formed, the masking material may be removed to expose the electrodes 130. In some instances, the outer cover 130 may be disposed over the electrodes 130 and subsequently removed, such as, but not limited to laser ablation. This may allow for the electrodes 326 to directly contact the vessel wall. It is further contemplated that the outer cover 130 may be removed from the electrodes 126 and the electrodes 126 independently (for example using parylene) for insulated contact with the desired treatment region.

In some embodiments, the inner and/or outer covers 122, 130 may include a plurality of holes or apertures (not explicitly shown) at the proximal and distal ends 116, 118 of the basket 114 to allow blood perfusion downstream of the system 100 while the basket 114 is expanded. This may also be preferred with insulated contact ablation to allow blood cooling of the intimal surface of the artery for the purpose of sparing the inside surface of the artery from ablation effects.

FIG. 3 illustrates the modulation system of FIGS. 2A-2D including an illustrative actuation mechanism 134 for actuating the basket 114 between a collapsed and an expanded position. The actuation mechanism 134 may include a handle or gripping portion 136 and a trigger portion 138. The trigger portion 138 may be affixed to a proximal end of the pull wire 132. As discussed above, a distal end of the pull wire 132 may be attached to or adjacent to the proximal end 116 or the distal end 118 of the basket. The actuation mechanism 134 may be configured such that actuation of the trigger portion 138 results in proximal and/or distal actuation of the pull wire 132 and subsequent expansion or contraction of the basket 114. While the actuation mechanism 134 is illustrated as including a handle 136 and trigger mechanism 138, it is contemplated that the pull wire 132 can be actuated in any manner desired, such as, but not limited to sliding mechanisms, buttons, etc.

The modulation system 100 may be advanced through the vasculature in any manner known in the art. For example, system 100 may include a guidewire lumen to allow the system 100 to be advanced over a previously located guidewire. In some embodiments, the modulation system 100 may be advanced, or partially advanced, within a guide sheath such as the sheath 14 shown in FIG. 1. Once the electrode assemblies 124a, 124b of the modulation system 100 have been placed adjacent to the desired treatment area, the expandable basket 114 may be expanded to bring the electrodes 126a, 126b into contact with the vessel wall.

It is contemplated that expansion of the basket 114 may be controlled such that consistent electrode contact with arterial wall may be accomplished. In some instances, the expanded diameter and/or cross-section of the basket 114 may be adjusted based on the size and/or shape of the vessel. For example, a physician may be able to partially expand the basket 114 in smaller vessels and fully expand the basket 114 in larger vessels. This may allow for fewer catheter sizes to be needed to treat the range of artery diameters (or cross-sectional areas) across patients and may allow for only one catheter to be needed in the approximately 25% of patients where left and right renal artery diameters vary by more than 1 millimeter (mm) since the basket 114 can be expanded to varying diameters. It is further contemplated that the expandable basket may reduce trauma to the arterial wall since the basket 114 would provide less apposition force while providing more complete apposition.

In some embodiments, the basket 114 may be designed to allow the electrode assemblies 124a, 124b to move to move radially independently of each other, allowing for better electrode 126a, 126b apposition as the vessel diameter changes along the length of the vessel. For example, the distal end 118 of the basket 114 could expand to a different cross-section than the proximal end 116 of the basket 114. In this instance, the basket 114 may expand to different degrees to generally conform to a vessel having a varying diameter along the length thereof. In some embodiments, the distal end 118 of the basket 114 may have a smaller or larger cross-section than the proximal end 116 of the basket 114. This may allow the modulation system 100 to be used in non-circumferential vessels as well as tapered vessels while still providing good electrode 126a, 126b contact.

While not explicitly shown, the electrode assemblies 124a, 124b may be connected to a single control unit or to separate control units (such as control unit 18 in FIG. 1) by electrical conductors 128a, 128b. Once the modulation system 100 has been advanced to the treatment region, energy may be supplied to the electrode assemblies 124a, 124b. The amount of energy delivered to the electrode assemblies 124a, 124b may be determined by the desired treatment as well as the feedback provided by other components of the system 100, such as, but not limited to, temperature sensors 127a, 127b.

Once a particular location has been ablated, it may be desirable to perform further ablation procedures at different longitudinal locations. Once the modulation system 100 has been longitudinally repositioned, energy may once again be delivered to the electrode assemblies 124a, 124b. If necessary, the modulation system may be rotated to perform ablation around the circumference of the vessel at each longitudinal location. This process may be repeated at any number of longitudinal locations desired.

When the modulation procedure has been completed, the basket 114 may be collapsed for withdrawal from the body. It is contemplated that basket 114 and electrode assemblies 124a, 124b may collapse in such a manner that "winging" may not occur. This may reduce the force required to withdraw the system 100. It is further contemplated that encasing all or part of the electrode assemblies 124a, 124b and the associated electronics may also reduce potential "catch" points on the modulation system 100 which may also reduce the force required to withdraw the system 100.

Figure 5:
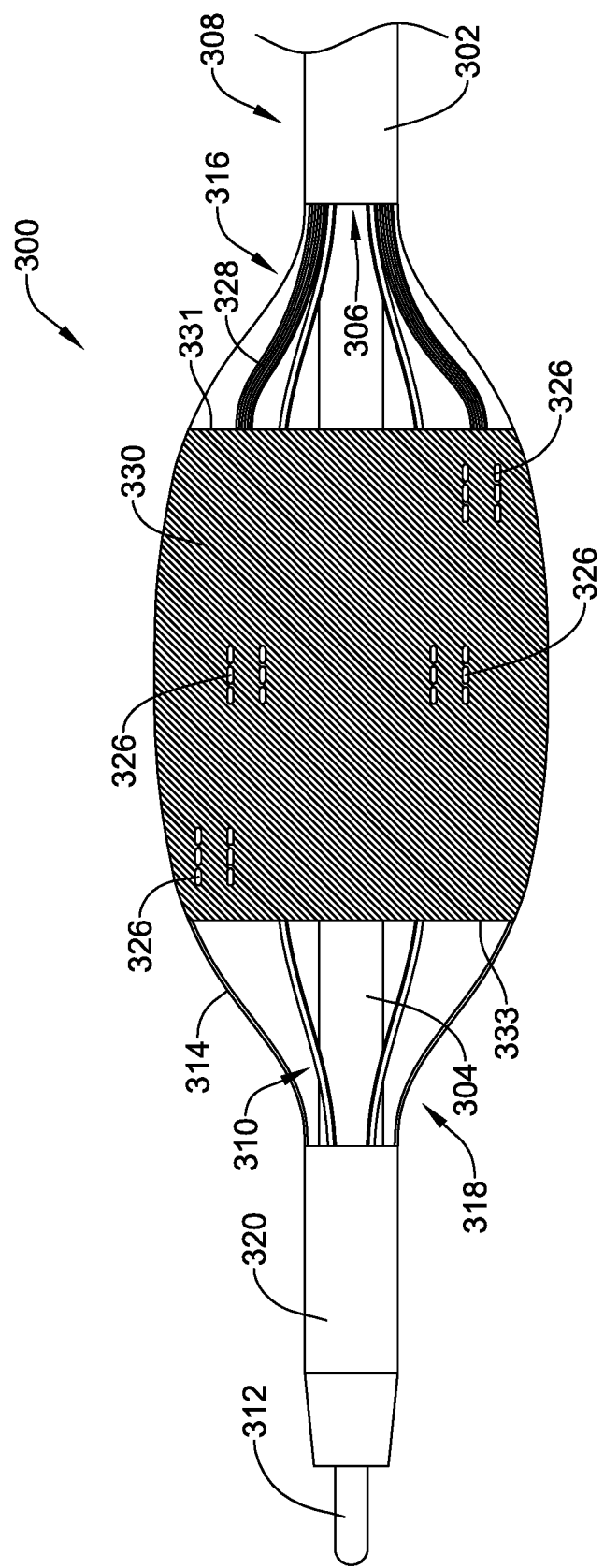
FIG. 5 illustrates a distal portion of another illustrative renal nerve modulation device.

FIG. 5 illustrates a distal portion of another illustrative renal nerve modulation device 300 having a basket structure covered with a coating. The renal nerve modulation system 300 may include an outer elongate shaft 302 having a proximal end and a distal end region 308. The outer elongate shaft 302 may extend proximally from the distal end region 308 to the proximal end configured to remain outside of a patient's body. The modulation device 300 may further include an inner elongate shaft 304 slidably disposed within a lumen 306 of the outer elongate shaft 302. The inner elongate shaft 304 may extend proximally from a distal end region 310 to a proximal end configured to remain outside of a patient's body. The inner tubular shaft 304 may include a lumen (not explicitly shown) having a guidewire wire 312 slidably disposed therein. In some instances, the modulation device 300 may have a fixed wire distal end with no guidewire lumen. Although not shown, the proximal ends of the inner and/or outer elongate shafts 304, 302 may include a hub attached thereto for connecting other treatment devices or providing a port for facilitating other treatments. It is contemplated that the stiffness of the inner and/or outer elongate shafts 304, 302 may be modified to form a modulation device 300 for use in various vessel diameters and various locations within the vascular tree. The inner and/or outer elongate shafts 304, 302 may be similar in form and function to the inner and/or outer elongate shafts 104, 102 described above.

The modulation device 300 may further include an expandable basket 314 having a proximal end 316 and a distal end 318. In some embodiments, the expandable basket 314 may be laser cut from a generally tubular member to form a desired pattern. While not explicitly shown, the expandable basket may have an open cell, generally stent-like, structure. In other instances, it is contemplated that the basket 314 may be formed to have any of a number of different configurations. For example, in some instances, the basket 314 may be formed from a number of generally longitudinally extending tines or may be formed from one or more filaments that may be woven, braided, knotted, etc. These are just examples. Basket 314 may be similar in form and function to basket 114 described above. Depending on the material selected for construction, the basket 314 may be self-expanding or may require an actuation mechanism such as actuation mechanism 134 described above.

The proximal end 316 of the basket 314 may be secured to or adjacent to the distal end region 308 of the outer elongate shaft 302. The distal end 318 of the basket 314 may be secured to or adjacent to the distal end region 310 of the inner elongate shaft 304. In some instances, the distal end 318 of the basket 314 may be secured directly to the inner elongate shaft 304. In other instances, the distal end 318 of the basket 314 may be secured to a mounting element 320. The mounting element 320 may be slidably disposed over the inner elongate shaft 304 or may be fixedly secured to the inner elongate shaft 304. As noted above, in some instances, the basket 314 may be self-expanding. It is contemplated that a self-expanding basket 314 may be maintained in a compressed (or collapsed state) when an external force is placed on the basket 314. The basket 314 may then expand when the external force is released. In such an instance, the basket 314 may be formed in the expanded state (as shown in FIG. 5) and compressed to fit within a delivery or capture sheath. Upon reaching the target location, the delivery sheath can be retracted to deploy the expandable basket 314. In some instances, a vascular access catheter can act as the capture sheath.

In other embodiments, the system 300 may include an actuation mechanism, such as actuation mechanism 134 described above, which may be employed to manipulate or actuate the expandable basket 314 between the collapsed and expanded configurations. In an embodiment, the pull wire may be attached to the proximal end 316 or distal end 318 of the basket 314 such that a push-pull actuation of the pull wire may manipulate the expandable basket 314, thus actuating the expandable basket 314 between the collapsed and expanded configurations. In some instances, the pull wire may be pulled proximally to pull the expandable basket 314, moving the expandable basket 314 to the expanded configuration. In addition, the pull wire may be pushed distally to move the expandable basket 314 into the collapsed configuration. Alternatively, the pull wire may be pushed distally, which may allow the expandable basket 314 to move to the expanded state. In such an instance, the pull wire may be pulled proximally, which may allow the expandable basket 314 to move to the collapsed state.

The modulation system 300 may further include an inner cover or coating (not explicitly shown) disposed on an inner surface of the expandable basket 314. It is contemplated that the inner cover may extend over any length or partial length of the basket 314 desired, or may not even be present. However, this is not required. It is contemplated that in some instances, the inner cover may extend from the proximal end 316 to the distal end 318 of the basket 314.

The modulation system 300 may further include one or more electrode assemblies (not explicitly shown) positioned on an outer surface of the expandable basket 314 and/or inner cover for delivering RF energy to a desired treatment region. The electrode assemblies may be similar in form and function to electrode assemblies 124a, 124b discussed above. However, the modulation systems disclosed herein are not intended to be limited to the use of only flexible circuits to deliver the treatment energy to the treatment region. It is contemplated that the energy delivery devices may be of any type desired. Electrodes 326 on the electrode assemblies may be connected to one another, other electrical components, and/or a power and control unit through one or more electrical conductors 328. The electrodes 326 may be operated in a bi-polar or monopolar mode as desired.

It is contemplated that the modulation system 300 may include any number of electrode assemblies desired based on the size of the modulation device 300 and/or the desired treatment region. For example, the modulation system may include one, two, three, four, five, or more electrode assemblies. It is further contemplated that the electrode assemblies may be staggered about the circumference and/or length of the expandable basket 314 such that a maximum number of electrode assemblies can be positioned on the modulation device.

The modulation system 300 may further include an outer cover or coating 330 disposed on an outer surface of the expandable basket 314 and over the inner cover (when so present). The outer cover 330 may be similar in form and function to outer cover 130 described above. It is contemplated that the outer cover 330 may have a proximal end 331 and a distal end 333. In some instances, the proximal end 331 of the cover 330 may be positioned distal to the proximal end 316 of the basket 314. It is further contemplated that the distal end 333 of the cover 330 may be positioned proximal to the distal end 318 of the basket 314. This may allow for blood perfusion downstream of the modulation system 300 during treatment. However, it is contemplated that either or both the proximal end 331 or the distal end 333 of the outer cover 330 may extend to the proximal or distal end 316, 318 of the frame 314. It is contemplated that the inner cover may have a similar configuration to the outer cover 330. The inner and outer covers 330 may be formed of the same material or may be formed from different materials, as desired. In some embodiments, one or both of the inner and/or outer covers 330 may be omitted.

In some instances, the outer cover 330 may be adhered to the inner cover and/or basket 314 using methods commonly known in the art. Together, the inner and outer covers 330 may encase all or part of the electrode assemblies and the associated electronics. It is contemplated that the inner and outer covers 330 may fix the electrode assemblies more securely to the expandable basket 314 relative to securing flex circuits to a traditional inflatable balloon as the inner and outer covers 330 sandwich the electrode assemblies and may be more amenable to covalent adhesive bonding. In some instances, the outer cover 330 may not extend over the electrodes 326 of the electrode assemblies. For example, the electrodes 326 may be coated or covered with a masking material prior to application of the outer cover 330. Once the outer cover 330 has been formed, the masking material may be removed to expose the electrodes 330. In some instances, the outer cover 330 may be disposed over the electrodes 330 and subsequently removed, such as, but not limited to laser ablation. This may allow for the electrodes 326 to directly contact the vessel wall. In other instances, the outer cover 330 may remain over the electrodes 326 to allow for insulated wall contact. It is further contemplated that the outer cover 330 may be removed from the electrodes 326 and the electrodes 326 independently coated (for example using parylene) for insulated contact with the desired treatment region.

Figure 6A:
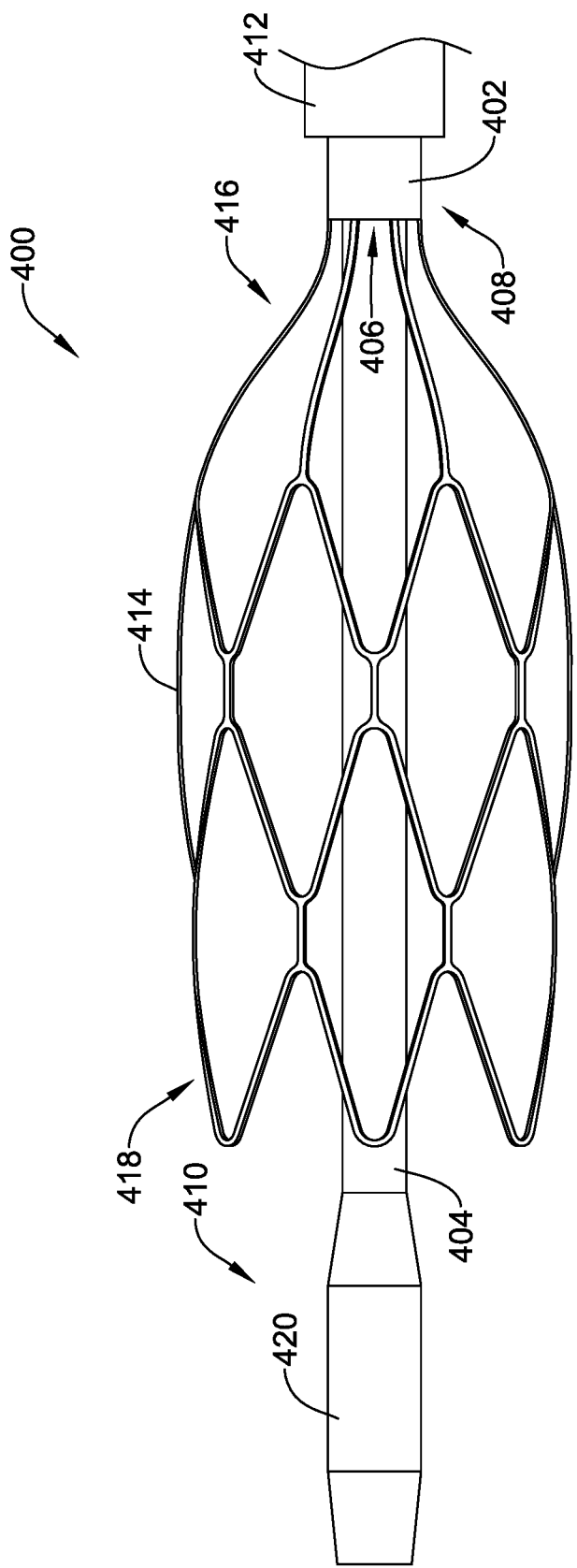
FIGS. 6A-6C illustrate a distal portion of another illustrative renal nerve modulation device.

FIGS. 6A-6C and 7 illustrate a distal portion of an illustrative renal nerve modulation device 400 having a basket structure covered with a coating. Referring first to FIG. 6A, the renal nerve modulation system 400 may include an outer elongate shaft 402 having a proximal end and a distal end region 408. The outer elongate shaft 402 may extend proximally from the distal end region 408 to the proximal end configured to remain outside of a patient's body. The modulation device 400 may further include an inner elongate shaft 404 having an atraumatic tip 420 slidably disposed within a lumen 406 of the outer elongate shaft 402. The inner elongate shaft 404 may extend proximally from a distal end region 410 to a proximal end configured to remain outside of a patient's body. Although not shown, the proximal ends of the inner and/or outer elongate shafts 404, 402 may include a hub attached thereto for connecting other treatment devices or providing a port for facilitating other treatments. It is contemplated that the stiffness of the inner and/or outer elongate shafts 404, 402 may be modified to form a modulation device 400 for use in various vessel diameters and various locations within the vascular tree.

In some instances, the inner and/or outer elongate shafts 404, 402 may have an elongate tubular structure and may include one or more lumens extending therethrough. For instance, in the illustrated embodiment, the outer elongate shaft 402 may include a lumen 406 for slidably receiving the inner tubular shaft 404. The inner tubular shaft 404 may include a lumen (not explicitly shown) for slidably receiving a guidewire wire therein. In some instances, the modulation device 400 may have a fixed wire distal end with no guidewire lumen. These are just examples. In some embodiments, the inner and/or outer elongate shafts 404, 402 may include one or more auxiliary lumens. In some instances, the inner and/or outer elongate shafts 404, 402 may include a separate lumen(s) (not shown) for infusion of fluids or for other purposes such as the introduction of a medical device, and so forth. The fluid may facilitate cooling of the modulation device 400 during the ablation procedure, in addition to the cooling of a body lumen. Further, the lumens may be configured in any way known in the art. For example, the lumen(s) may extend along the entire length of the inner and/or outer elongate shafts 404, 402 such as in an over-the-wire catheter or may extend only along a distal portion of the inner and/or outer elongate shafts 404, 402 such as in a single operator exchange (SOE) catheter. These examples are not intended to be limiting, but rather examples of some possible configurations. While not explicitly shown, the modulation device 400 may further include temperature sensors/wire, an infusion lumen, radiopaque marker bands, fixed guidewire tip, a guidewire lumen, and/or other components to facilitate the use and advancement of the device 400 within the vasculature.

Further, the inner and/or outer elongate shafts 404, 402 may have a relatively long, thin, flexible tubular configuration. In some instances, the inner and/or outer elongate shafts 404, 402 may have a generally circular cross-section, however, other suitable configurations such as, but not limited to, rectangular, oval, irregular, or the like may also be contemplated. In addition, the inner and/or outer elongate shafts 404, 402 may have a cross-sectional configuration adapted to be received in a desired vessel, such as a renal artery. For instance, the inner and/or outer elongate shafts 404, 402 may be sized and configured to accommodate passage through an intravascular path, which leads from a percutaneous access site in, for example, the femoral, brachial, or radial artery, to a targeted treatment site, for example, within a renal artery.

The modulation device 400 may further include an expandable basket 414 having a proximal end 416 and a distal end 418. In some instances, in the expanded state, the proximal end 416 may be tapered while the distal end 418 may have an enlarged cross-sectional area relative to the proximal end 416. In some embodiments, the expandable basket 414 may be laser cut from a generally tubular member to form the desired pattern. While the expandable basket 414 is illustrated as having an open cell, generally stent-like, structure it is contemplated that the basket 414 may be formed to have any of a number of different configurations. For example, in some instances, the basket 414 may be formed from a number of generally longitudinally extending tines or may be formed from one or more filaments that may be woven, braided, knotted, etc. These are just examples.

It is contemplated that the expandable basket 414 can be made from a number of different materials such as, but not limited to, metals, metal alloys, shape memory alloys and/or polymers, as desired, enabling the basket 414 to be expanded into shape when positioned within the body. For example, the expandable basket 414 can be formed from alloys such as, but not limited to, nitinol or Elgiloy®. Depending on the material selected for construction, the basket 414 may be self-expanding or may require an actuation mechanism as will be discussed in more detail below. In some embodiments, fibers may be used to make the expandable basket 414, which may be cored fibers, for example, having an outer shell made of nitinol having a platinum core. It is further contemplated the expandable basket 414 may be formed from polymers including, but not limited to, polyether ether ketone (PEEK), nylon, polyethylene terephthalate (PET), polyimides, polyether block amides, etc.

The proximal end 416 of the basket 414 may be secured to or adjacent to the distal end region 408 of the outer elongate shaft 402. As noted above, in some instances, the basket 414 may be self-expanding. It is contemplated that a self-expanding basket 414 may be maintained in a compressed (or collapsed state) when an external force is placed on the basket 414. The basket 414 may then expand when the external force is released. In such an instance, the basket 414 may be formed in the expanded state (as shown in FIG. 2A) and compressed to fit within a delivery sheath 412. Upon reaching the target location, the delivery sheath 412 can be retracted to deploy the expandable basket 414.

In other embodiments, the system 400 may include an actuation mechanism, for example, a pull wire 432 (see FIG. 7), which may be employed to manipulate or actuate the expandable basket 414 between the collapsed and expanded configurations. In an embodiment, the pull wire 432 may be attached to the proximal end 416 of the basket 414 such that a push-pull actuation of the pull wire 432 may manipulate the expandable basket 414, thus actuating the expandable basket 414 between the collapsed and expanded configurations. In some instances, the pull wire 432 may be pulled proximally to pull the expandable basket 414, moving the expandable basket 414 to the expanded configuration. In addition, the pull wire 432 may be pushed distally to move the expandable basket 414 into the collapsed configuration. Alternatively, the pull wire 432 may be pushed distally, which may allow the expandable basket 414 to move to the expanded state. In such an instance, the pull wire 432 may be pulled proximally, which may allow the expandable basket 414 to move to the collapsed state.

Figure 6B:
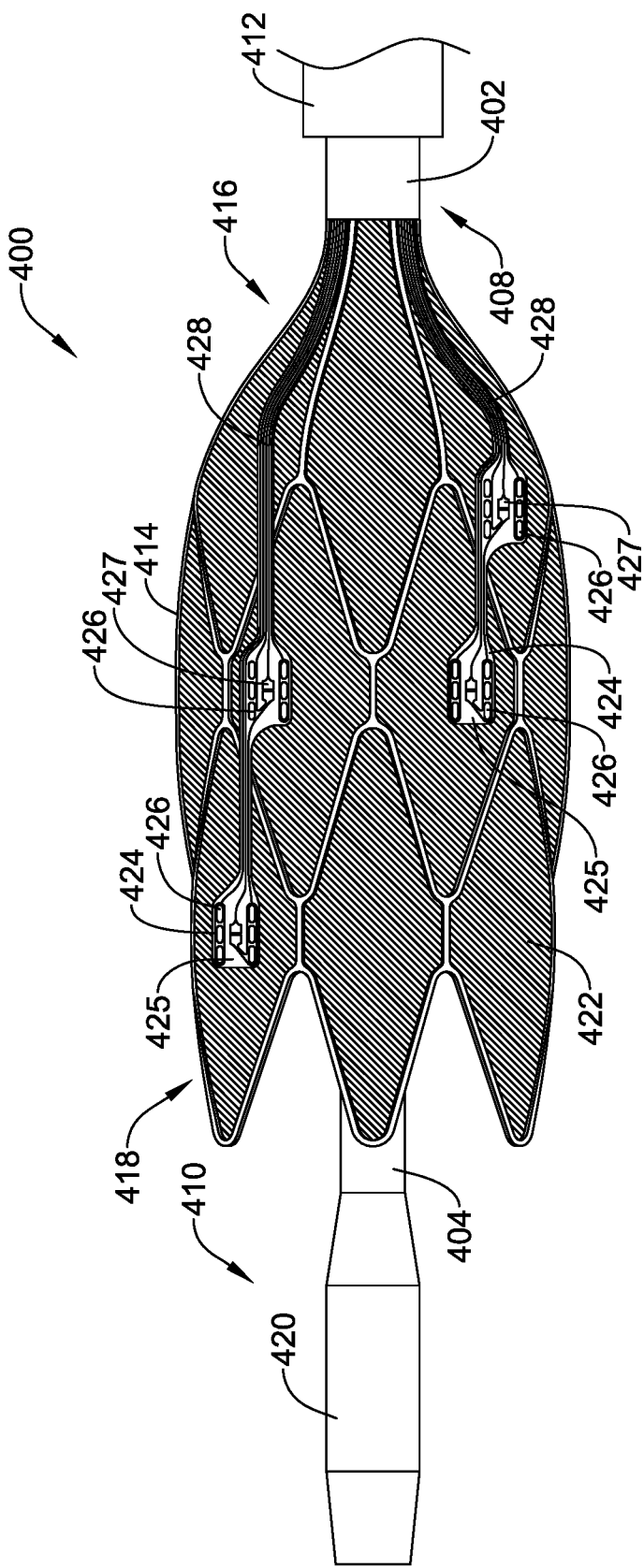

FIG. 6B illustrates the modulation system 400 of FIG. 6A including additional components. The modulation system 400 may further include an inner cover or coating 422 disposed on an inner surface of the expandable basket 414. In some instances, the inner cover 422 may be adhered to the basket 414 using methods commonly known in the art. The inner cover 422 may be made from an elastomeric material, such as, but not limited to: polyurethane, silicone, etc. An elastomeric material may help close the basket 414 to its un-expanded configuration after use. However, in some instances, elastomers such as polyurethane may fail due the heat from ablation. To prevent this, the elastomer could be insulated around the electrodes with a higher temperature material, doped to increase its melt point, (for example, with silica), one may use higher temperature urethanes (for example, aromatics that are dip coated rather than extruded). Alternatively, the cover material could be a less stretchable material, for example, tetrafluoroethylene (Tfe), polyethylene terephthalate (PET), or fabrics (for example, polyester or polymer coated fabrics), which would be less subject to the ablation temperatures. It is contemplated that the inner cover 422 may extend from the proximal end 416 to the distal end 418 of the basket 414. However, this is not required. It is contemplated that the inner cover 422 may extend over any length or partial length of the basket 414 desired, or may not even be present.

The modulation system 400 may further include one or more electrode assemblies 424 positioned on an outer surface of the expandable basket 414 and/or inner cover 422 for delivering RF energy to a desired treatment region. An exemplary electrode assembly useable with the embodiments disclosed herein is disclosed in U.S. Patent Application Ser. No. 61/856,523 entitled "Spiral Bipolar Electrode Renal Denervation Balloon", the full disclosure of which is incorporated by reference herein. The electrodes assemblies 424 may be similar in form and function to electrodes assemblies 124a, 124b discussed above. Each electrode assembly 424 may be constructed as a flexible circuit having a plurality of layers. A base layer 425 of insulation may provide a foundation for the electrode assemblies 424. The base layer 425 may be constructed from a flexible polymer such as polyimide, although other materials are contemplated. However, the modulation systems disclosed herein are not intended to be limited to the use of only flexible circuits to deliver the treatment energy to the treatment region. It is contemplated that the energy delivery devices may be of any type desired. A conductive layer made up of a plurality of discrete traces may be layered on top of the base layer 425. The electrode assemblies 424 may include a plurality of discrete traces 428 layered on top of the base layer 425. These traces may include a ground trace, an active electrode trace, and a sensor trace (not explicitly shown) for electrically connecting electrodes, components, and/or a power and control unit. The ground electrode trace and active electrode trace may include a plurality of electrodes 426. Three electrodes 426 may be provided for each electrode trace, however, more or less may be used. Additionally, one or more temperature sensors 427 may be provided on each electrode assembly 424.

It is contemplated that the modulation system 400 may include any number of electrode assemblies 424 desired based on the size of the modulation device 400 and/or the desired treatment region. For example, the modulation system may include one, two, three, four, five, or more electrode assemblies. It is further contemplated that the electrode assemblies 424 may be staggered about the circumference and/or length of the expandable basket 414 such that a maximum number of electrode assemblies 424 can be positioned on the modulation device.

Figure 6C:
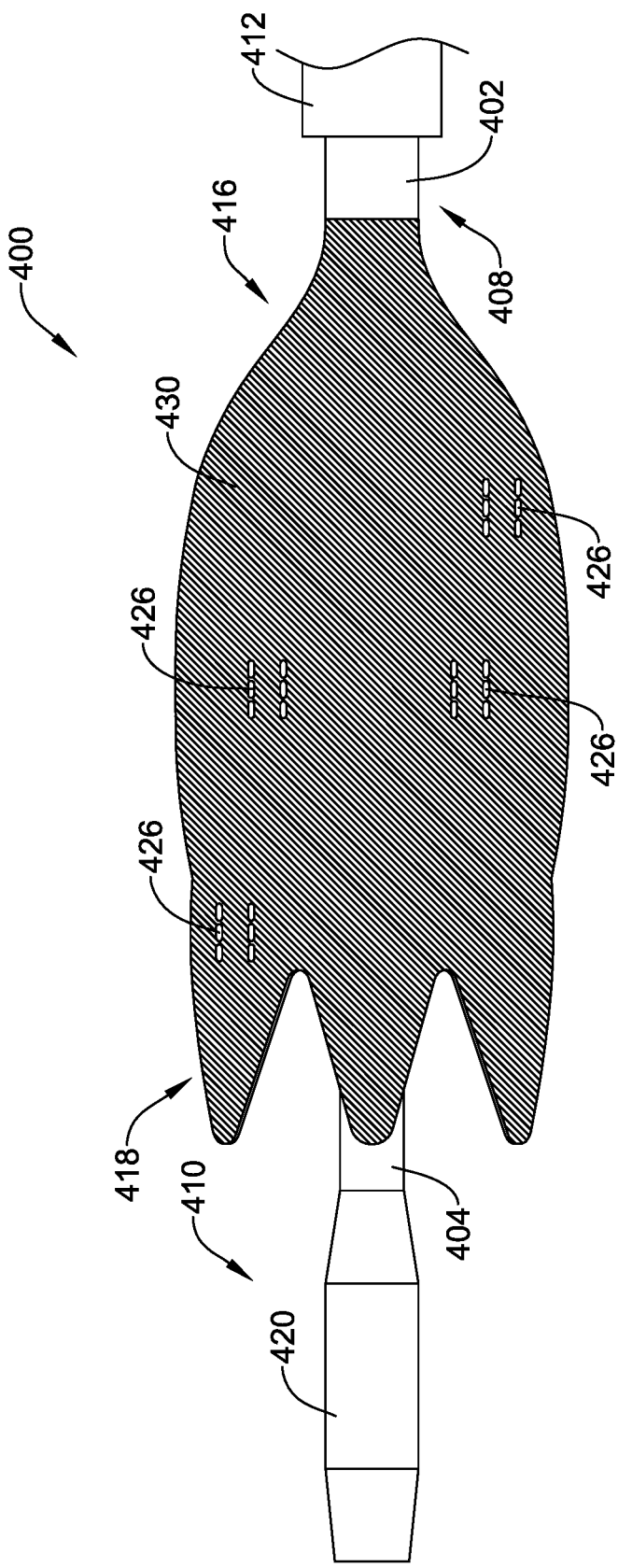

FIG. 6C illustrates the modulation system 400 of FIG. 6B including additional components. The modulation system 400 may further include an outer cover or coating 430 disposed on an outer surface of the expandable basket 414 and over the inner cover 422, when so present. The outer cover 430 may be made from an elastomeric material, such as, but not limited to: polyurethane, silicone, etc. An elastomeric material may help close the basket 414 to its un-expanded configuration after use. However, in some instances, elastomers such as polyurethane may fail due the heat from ablation. To prevent this, the elastomer could be insulated around the electrodes with a higher temperature material, doped to increase its melt point, (for example, silica), or it may be fine using higher temperature urethanes (for example, aromatics that are dip coated rather than extruded). Alternatively, the cover material could be a less stretchable material, for example, tetrafluoroethylene (Tfe), polyethylene terephthalate (PET), or fabrics (for example, polyester or polymer coated fabrics), which would be less subject to the ablation temperatures. It is contemplated that the outer cover 430 may extend from the proximal end 416 to the distal end 418 of the basket 414. However, this is not required. It is contemplated that the outer cover 430 may extend over any length or partial length of the basket 414 desired, or may not even be present. The inner and outer covers 422, 430 may be formed of the same material or may be formed from different materials, as desired. In some embodiments, one or both of the inner and/or outer covers 422, 430 may be omitted.

In some instances, the outer cover 430 may be adhered to the inner cover 422 and/or basket 414 using methods commonly known in the art. Together, the inner and outer covers 422, 430 may encase all or part of the electrode assemblies 424 and the associated electronics. It is contemplated that the inner and outer covers 422, 430 may fix the electrode assemblies 424 more securely to the expandable basket 414 relative to securing flex circuits to a traditional inflatable balloon as the inner and outer covers 422, 430 sandwich the electrode assemblies 424 and may be more amenable to covalent adhesive bonding.

In some instances, the outer cover 430 may not extend over the electrodes 426 of the electrode assemblies 42. For example, the electrodes 426 may be coated or covered with a masking material prior to application of the outer cover 430. Once the outer cover 430 has been formed, the masking material may be removed to expose the electrodes 430. In some instances, the outer cover 430 may be disposed over the electrodes 430 and subsequently removed, such as, but not limited to laser ablation. This may allow for the electrodes 426 to directly contact the vessel wall. In other instances, the outer cover 430 may remain over the electrodes 426 to allow for insulated wall contact. It is further contemplated that the outer cover 430 may be removed from the electrodes 426 and the electrodes 426 independently coated (for example using parylene) for insulated contact with the desired treatment region.

Figure 7:
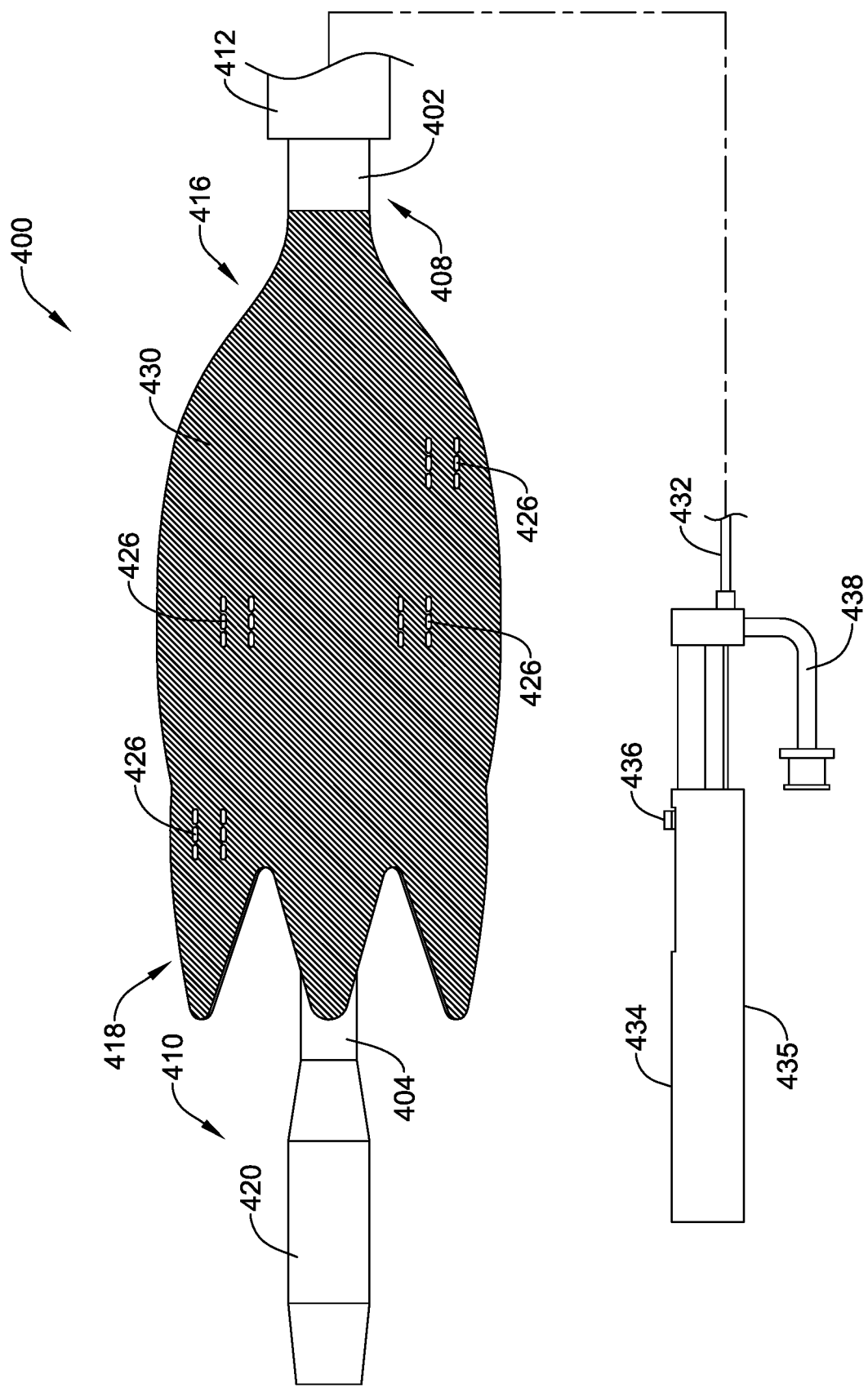
FIG. 7 illustrates the illustrative renal nerve modulation device of FIGS. 6A-6C including an actuation mechanism.

FIG. 7 illustrates the modulation system of FIGS. 6A-6C including an illustrative actuation mechanism 434 for actuating the basket 414 between a collapsed and an expanded position. The actuation mechanism 434 may include a handle or gripping portion 435 and a sliding mechanism 436. The sliding mechanism 436 may be affixed to a proximal end of the pull wire 432. As discussed above, a distal end of the pull wire 432 may be attached to or adjacent to the proximal end 416 of the basket. The actuation mechanism 434 may be configured such that actuation of the sliding mechanism 436 results in proximal and/or distal actuation of the pull wire 432 and subsequent expansion or contraction of the basket 414. While the actuation mechanism 434 is illustrated as including a handle 435 and sliding mechanism 436, it is contemplated that the pull wire 432 can be actuated in any manner desired, such as, but not limited to triggers, buttons, etc. For example, the actuation mechanism 434 may be similar in form and function to actuation mechanism 134 described above.

Figure 8:
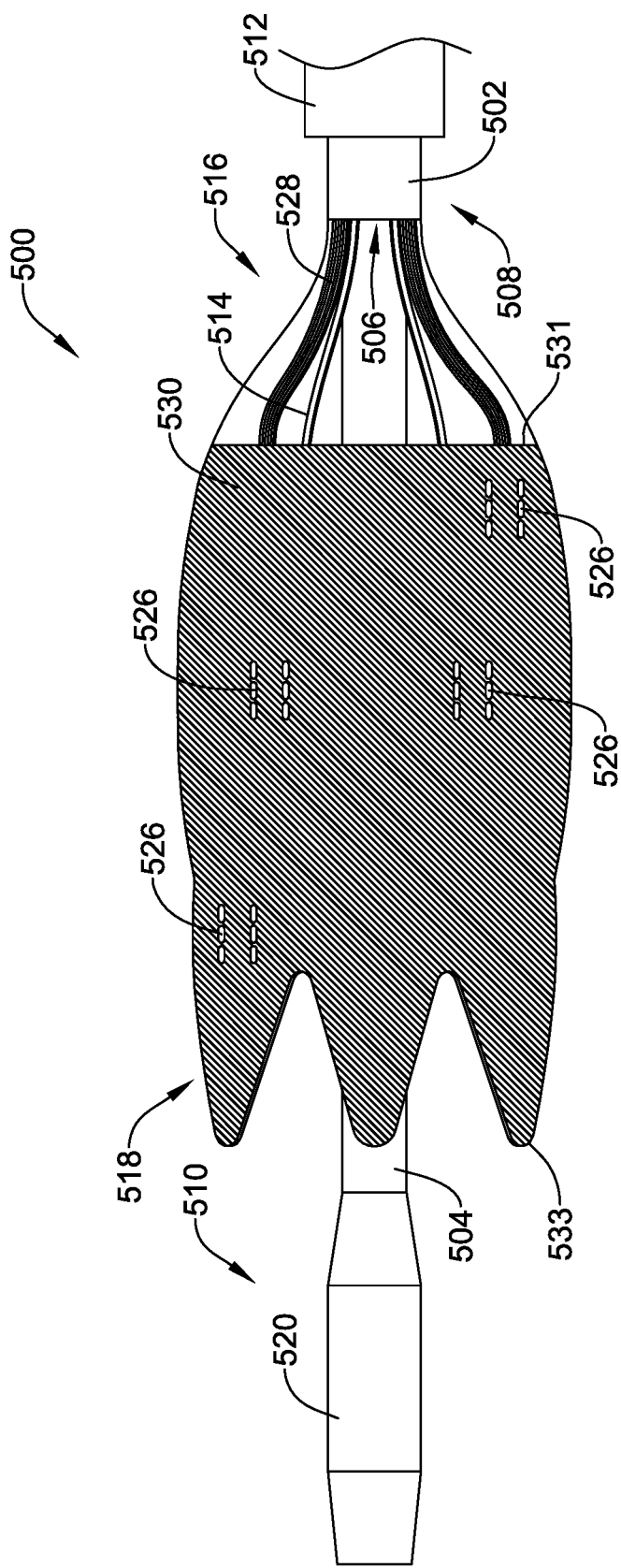
FIG. 8 illustrates a distal portion of another illustrative renal nerve modulation device.

FIG. 8 illustrates a distal portion of another illustrative renal nerve modulation device 500 having a basket structure covered with a coating. The renal nerve modulation system 500 may include an outer elongate shaft 502 having a proximal end and a distal end region 508. The outer elongate shaft 502 may extend proximally from the distal end region 508 to the proximal end configured to remain outside of a patient's body. The modulation device 500 may further include an inner elongate shaft 504 having an atraumatic tip 520 slidably disposed within a lumen 506 of the outer elongate shaft 502. The inner elongate shaft 504 may extend proximally from a distal end region 510 to a proximal end configured to remain outside of a patient's body. The inner tubular shaft 504 may include a lumen (not explicitly shown) for slidably receiving a guidewire wire therein. In some instances, the modulation device 500 may have a fixed wire distal end with no guidewire lumen. Although not shown, the proximal ends of the inner and/or outer elongate shafts 504, 502 may include a hub attached thereto for connecting other treatment devices or providing a port for facilitating other treatments. It is contemplated that the stiffness of the inner and/or outer elongate shafts 504, 502 may be modified to form a modulation device 500 for use in various vessel diameters and various locations within the vascular tree. The inner and/or outer elongate shafts 504, 502 may be similar in form and function to the inner and/or outer elongate shafts 104, 404, 102, 402 described above.

The modulation device 500 may further include an expandable basket 514 having a proximal end 516 and a distal end 518. In some instances, in the expanded state, the proximal end 516 may be tapered while the distal end 518 may have an enlarged cross-sectional area relative to the proximal end 516. In some embodiments, the expandable basket 514 may be laser cut from a generally tubular member to form a desired pattern. While not explicitly shown, the expandable basket may have an open cell, generally stent-like, structure. In other instances, it is contemplated that the basket 514 may be formed to have any of a number of different configurations. For example, in some instances, the basket 514 may be formed from a number of generally longitudinally extending tines or may be formed from one or more filaments that may be woven, braided, knotted, etc. These are just examples. Basket 514 may be similar in form and function to basket 414 described above. Depending on the material selected for construction, the basket 514 may be self-expanding or may require an actuation mechanism such as actuation mechanism 134, 434 described above.

The proximal end 516 of the basket 514 may be secured to or adjacent to the distal end region 508 of the outer elongate shaft 502. As noted above, in some instances, the basket 514 may be self-expanding. It is contemplated that a self-expanding basket 514 may be maintained in a compressed (or collapsed state) when an external force is placed on the basket 514. The basket 514 may then expand when the external force is released. In such an instance, the basket 514 may be formed in the expanded state (as shown in FIG. 8) and compressed to fit within a delivery sheath 512. Upon reaching the target location, the delivery sheath 512 can be retracted to deploy the expandable basket 514.

In other embodiments, the system 500 may include an actuation mechanism, such as actuation mechanism 134, 434 described above, which may be employed to manipulate or actuate the expandable basket 514 between the collapsed and expanded configurations. In an embodiment, a pull wire may be attached to the proximal end 516 of the basket 514 such that a push-pull actuation of the pull wire may manipulate the expandable basket 514, thus actuating the expandable basket 514 between the collapsed and expanded configurations. In some instances, the pull wire may be pulled proximally to pull the expandable basket 514, moving the expandable basket 514 to the expanded configuration. In addition, the pull wire may be pushed distally to move the expandable basket 514 into the collapsed configuration. Alternatively, the pull wire may be pushed distally, which may allow the expandable basket 514 to move to the expanded state. In such an instance, the pull wire may be pulled proximally, which may allow the expandable basket 514 to move to the collapsed state.

The modulation system 500 may further include an inner cover or coating (not explicitly shown) disposed on an inner surface of the expandable basket 514. It is contemplated that the inner cover may extend over any length or partial length of the basket 514 desired, or may not even be present. However, this is not required. It is contemplated that in some instances, the inner cover may extend from the proximal end 516 to the distal end 518 of the basket 514.

The modulation system 500 may further include one or more electrode assemblies (not explicitly shown) positioned on an outer surface of the expandable basket 514 and/or inner cover for delivering RF energy to a desired treatment region. The electrode assemblies may be similar in form and function to electrode assemblies 124a, 124b discussed above. However, the modulation systems disclosed herein are not intended to be limited to the use of only flexible circuits to deliver the treatment energy to the treatment region. It is contemplated that the energy delivery devices may be of any type desired. Electrodes 526 on the electrode assemblies may be connected to one another, other electrical components, and/or a power and control unit through one or more electrical conductors 528. The electrodes 526 may be operated in a bi-polar or monopolar mode as desired.

It is contemplated that the modulation system 500 may include any number of electrode assemblies desired based on the size of the modulation device 500 and/or the desired treatment region. For example, the modulation system may include one, two, three, four, five, or more electrode assemblies. It is further contemplated that the electrode assemblies may be staggered about the circumference and/or length of the expandable basket 514 such that a maximum number of electrode assemblies can be positioned on the modulation device.

The modulation system 500 may further include an outer cover or coating 530 disposed on an outer surface of the expandable basket 514 and over the inner cover (when so present). The outer cover 530 may be similar in form and function to outer covers 130, 430 described above. It is contemplated that the outer cover 530 may have a proximal end 531 and a distal end 533. In some instances, the proximal end 531 of the cover 530 may be positioned distal to the proximal end 516 of the basket 514. It is further contemplated that the distal end 533 of the cover 530 may be positioned proximal to the distal end 518 of the basket 514 or may extend to the distal end 518 of the basket 514. This may allow for blood perfusion downstream of the modulation system 500 during treatment. However, it is contemplated that either or both the proximal end 531 or the distal end 533 of the outer cover 530 may extend to the proximal or distal end 516, 518 of the frame 514 as desired. It is contemplated that the inner cover may have a similar configuration to the outer cover 530. The inner and outer covers 530 may be formed of the same material or may be formed from different materials, as desired. In some embodiments, one or both of the inner and/or outer covers 530 may be omitted.

In some instances, the outer cover 530 may be adhered to the inner cover and or basket 514 using methods commonly known in the art. Together, the inner and outer covers 530 may encase all or part of the electrode assemblies and the associated electronics. It is contemplated that the inner and outer covers 530 may fix the electrode assemblies more securely to the expandable basket 514 relative to securing flex circuits to a traditional inflatable balloon as the inner and outer covers 530 sandwich the electrode assemblies and may be more amenable to covalent adhesive bonding. In some instances, the outer cover 530 may not extend over the electrodes 526 of the electrode assemblies. For example, the electrodes 526 may be coated or covered with a masking material prior to application of the outer cover 530. Once the outer cover 530 has been formed, the masking material may be removed to expose the electrodes 530. In some instances, the outer cover 530 may be disposed over the electrodes 530 and subsequently removed, such as, but not limited to laser ablation. This may allow for the electrodes 526 to directly contact the vessel wall. In other instances, the outer cover 530 may remain over the electrodes 526 to allow for insulated wall contact. It is further contemplated that the outer cover 530 may be removed from the electrodes 526 and the electrodes 526 independently coated (for example using parylene) for insulated contact with the desired treatment region.

The materials that can be used for the various components of the modulation systems 100, 300, 400, 500 (and/or other devices disclosed herein) may include those commonly associated with medical devices. For simplicity purposes, the following discussion makes reference to the modulation systems 100, 300, 400, 500. However, this is not intended to limit the devices and methods described herein, as the discussion may be applied to other similar tubular members and/or expandable members and/or components of tubular members and/or expandable members disclosed herein.

The modulation systems 100, 300, 400, 500 and the various components thereof may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions of the modulation systems 100, 300, 400, 500 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the modulation systems 100, 300, 400, 500 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the modulation systems 100, 300, 400, 500 to achieve the same result.

In some embodiments, a degree of Magnetic Resonance Imaging (MRI) compatibility may be imparted into the modulation systems 100, 300, 400, 500. For example, portions of the modulation systems 100, 300, 400, 500 may be made of a material that does not substantially distort the image and create substantial artifacts (i.e., gaps in the image). Certain ferromagnetic materials, for example, may not be suitable because they may create artifacts in an MRI image. In some of these and in other embodiments, portions of the modulation systems 100, 300, 400, 500 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A system, comprising:
an outer elongate shaft having a proximal end, a distal end, and a lumen extending therebetween;
an inner elongate shaft having a proximal end and a distal end;
an expandable basket having a proximal end and a distal end, the proximal end of the expandable basket affixed adjacent to the distal end of the outer elongate shaft;
an electrode assembly comprising one or more electrodes affixed adjacent to the expandable basket;
an inner cover disposed over an inner surface of the expandable basket;
an outer cover disposed over the outer surface of the expandable basket; and
wherein the one or more electrodes are disposed between the inner cover and the outer cover.

2. The system of claim 1, wherein the electrode assembly is affixed to a surface of the inner cover.

3. The system of claim 1, wherein the outer cover and the inner cover comprise an elastomeric material.

4. The system of claim 3, wherein the outer cover and the inner cover comprise the same elastomeric material.

5. The system of claim 3, wherein the outer cover and the inner cover comprise different elastomeric materials.

6. The system of claim 1, wherein the electrode assembly is affixed to an outer surface of the expandable basket.

7. The system of claim 1, wherein the electrode assembly is affixed to an inner surface of the outer cover.

8. A system, comprising:
an outer elongate shaft having a proximal end, a distal end, and a lumen extending therebetween;
an inner elongate shaft having a proximal end and a distal end;
an expandable basket having a proximal end and a distal end, the proximal end of the expandable basket affixed adjacent to the distal end of the outer elongate shaft and the distal end of the expandable basket affixed adjacent to the distal end of the inner elongate shaft;
an electrode assembly comprising one or more electrodes affixed to an outer surface of the expandable basket, the electrode assembly constructed as a flexible circuit comprising a flexible polymer base layer and a conductive layer comprising a plurality of conductive traces disposed over the base layer; and
an outer cover disposed over the outer surface of the expandable basket and at least a portion of the electrode assembly;
wherein the inner elongate shaft and outer elongate shaft are slidable relative to each other to transition the expandable basket between a collapsed configuration and an expanded configuration; and
wherein openings are provided in the outer cover, at the proximal and distal ends of the expandable basket such that fluid is allowed to perfuse downstream of the system while the basket is in the expanded configuration.

9. The system of claim 8, wherein in the expanded configuration, the distal end of the expandable basket and the proximal end of the expandable basket have a tapered cross-sectional area.

10. The system of claim 8, further comprising one or more additional electrode assemblies.

11. The system of claim 10, wherein the electrode assembly and the one or more additional electrode assemblies are spaced about a circumference of the expandable basket.

12. The system of claim 8, wherein the outer cover does not extend over the electrodes of the electrode assemblies.

13. The system of claim 8, wherein the electrodes of the electrode assemblies are covered and configured for insulated contact with a surrounding treatment region.

14. A system, comprising:
an outer elongate shaft having a proximal end, a distal end, and a lumen extending therebetween;
an inner elongate shaft having a proximal end and a distal end;
an expandable basket having a proximal end and an open distal end, the proximal end of the expandable basket affixed adjacent to the distal end of the outer elongate shaft;
an electrode assembly comprising one or more electrodes affixed to an outer surface of the expandable basket, the electrode assembly constructed as a flexible circuit comprising a flexible polymer base layer and a conductive layer comprising a plurality of conductive traces disposed over the base layer; and
an outer cover disposed over the outer surface of the expandable basket and at least a portion of the electrode assembly;
wherein the electrode assembly is affixed to an inner surface of the outer cover.

15. The system of claim 14, wherein the outer cover extends over the electrodes of the electrode assemblies and the electrodes are configured for insulated contact with a surrounding treatment region.

16. The system of claim 14, wherein the outer cover does not extend over the electrodes of the electrode assemblies.

17. The system of claim 14, wherein the outer cover comprises an elastomeric material.

* * * * *